(12) United States Patent
Kilian et al.

(10) Patent No.: US 7,714,886 B2
(45) Date of Patent: May 11, 2010

(54) SYSTEMS AND METHODS FOR OBTAINING IMPROVED ACCURACY MEASUREMENTS OF MOVING ROLLING STOCK COMPONENTS

(75) Inventors: Krzysztof Kilian, Colorado Springs, CO (US); Vladimir Mazur, Floreat (AU)

(73) Assignee: LynxRail Corporation, Colorado Springs, CO (US)

( * ) Notice: Subject to any disclaimer, the term of this patent is extended or adjusted under 35 U.S.C. 154(b) by 901 days.

(21) Appl. No.: 11/370,015

(22) Filed: Mar. 7, 2006

(65) Prior Publication Data

US 2007/0211145 A1  Sep. 13, 2007

(51) Int. Cl.
 *H04N 7/18* (2006.01)
(52) U.S. Cl. ...................................... 348/135
(58) Field of Classification Search ................. 348/135, 348/155, 170; 702/157, 151; 73/865.3, 129; *H04N 7/81*
 See application file for complete search history.

(56) References Cited

U.S. PATENT DOCUMENTS

| | | | |
|---|---|---|---|
| 3,206,596 A | | 9/1965 | Howell |
| 3,253,140 A | | 5/1966 | Sibley et al. |
| 4,798,964 A | | 1/1989 | Schmalfuss et al. |
| 4,866,642 A | * | 9/1989 | Obrig et al. ................ 702/157 |
| 5,247,338 A | | 9/1993 | Danneskiold-Samsoe et al. |
| 5,327,782 A | * | 7/1994 | Sato et al. ...................... 73/129 |
| 5,448,072 A | | 9/1995 | Gallagher |
| 5,574,233 A | * | 11/1996 | Oliver et al. ............... 73/865.8 |
| 5,596,203 A | | 1/1997 | Zingarelli et al. |
| 5,636,026 A | * | 6/1997 | Mian et al. .................. 356/602 |
| 5,677,533 A | | 10/1997 | Yaktine et al. |
| 5,793,492 A | | 8/1998 | Vanaki |
| 5,808,906 A | * | 9/1998 | Sanchez-Revuelta et al. ........................... 702/151 |
| 6,088,635 A | * | 7/2000 | Cox et al. ...................... 701/19 |
| 6,768,551 B2 | | 7/2004 | Mian et al. |
| 6,823,242 B1 | | 11/2004 | Ralph |
| 6,872,945 B2 | | 3/2005 | Bartonek |
| 6,909,514 B2 | * | 6/2005 | Nayebi ....................... 356/601 |
| 6,911,914 B2 | | 6/2005 | Mathews, Jr. et al. |
| 7,152,347 B2 | * | 12/2006 | Herzog et al. ................. 37/195 |
| 7,328,871 B2 | * | 2/2008 | Mace et al. ............. 246/169 R |
| 2005/0278982 A1 | * | 12/2005 | Herzog et al. ................. 37/104 |
| 2006/0010971 A1 | | 1/2006 | Kilian et al. |

(Continued)

FOREIGN PATENT DOCUMENTS

WO  WO 2006/010154 A2  1/2006

*Primary Examiner*—Tung Vo
(74) *Attorney, Agent, or Firm*—Lathrop & Clark LLP

(57) ABSTRACT

Reference markers are attached to rails and/or other dynamically moving components of railroad tracks, and/or located at fixed and stationary positions adjacent to the track. When images of railway rolling stock are obtained, the reference marker(s) appear in the image. Accordingly, measurements of various aspects and parameters of various components of the railway rolling stock can be obtained at high precision and/or accuracy relative to the railroad track component to which the reference marker is attached and/or relative to the stationary position. The reference markers allow one or more images, obtained at some intervening time interval, to be accurately and precisely aligned relative to the reference marker(s) regardless of the dynamic motion of the railroad track component(s) and/or of the rolling stock that occurred as the images were captured. The reference markers can include optical, thermal or other indicia. The indicia have known dimensions and/or known distances from an image capture device.

17 Claims, 16 Drawing Sheets

U.S. PATENT DOCUMENTS

2006/0017911 A1* 1/2006 Villar et al. ................. 356/4.01
2007/0062763 A1* 3/2007 Shiratsuki et al. ........... 187/394
2007/0064244 A1* 3/2007 Mian et al. .................. 356/601
2007/0129858 A1* 6/2007 Herzog et al. ................. 701/19
2007/0137514 A1* 6/2007 Kumar et al. ............ 105/26.05

* cited by examiner

SYSTEMS AND METHODS FOR OBTAINING IMPROVED ACCURACY MEASUREMENTS OF MOVING ROLLING STOCK COMPONENTS

BACKGROUND OF THE INVENTION

1. Field of the Invention

This invention is directed to obtaining higher accuracy measurements of the rolling stock of a railroad.

2. Related Art

The rolling stock of a railroad, such as box cars, flat cars, tanker cars, hopper cars, gondolas, piggy back carriers for semi-tractor trailers and/or containers, passenger cars, and the like, are subject to wear, fatigue and the like. This is especially true of the wheels and trucks of such rolling stock. Accordingly, it is typically necessary or desirable to inspect such rolling stock, and especially the trucks and wheels of such rolling stock, on occasion to insure that the rolling stock remains safe to use and is not likely to experience a breakdown in the interval between the current inspection and the next inspection of that piece of rolling stock.

Traditionally, such inspections were performed manually. Not only was such manual inspection time consuming and expensive, it was difficult to insure that a given piece of rolling stock was inspected on any reasonable schedule.

Accordingly, as set forth in U.S. Pat. Nos. 6,911,914; 6,909,514; 6,872,945; 6,823,242; 6,768,551; 5,793,492; 5,677,533; 5,596,203; 5,448,072; 5,247,338; 3,253,140; and 3,206,596, each of which is incorporated herein by reference for its teachings, over the last thirty years, various systems and methods have been developed for automatically inspecting various aspects and parameters of railway rolling stock, such as railroad wheel and bearing temperatures, hot rail car surfaces, wheel profiles, and the like. Conventionally, such systems and methods have used passive sensors that generate a 1-dimensional, time-varying signal as the piece of rolling stock passes by the sensor. To provide additional dimensional information, multiple sensors can be arranged either along or perpendicular to the railway rail. More recently, optical-based systems that generate 2-dimensional images of various components of railway rolling stock, such as wheels, truck assemblies, car bodies of the rolling stock and the like, have been used to inspect such rolling stock.

SUMMARY OF THE DISCLOSED EMBODIMENTS

Such systems and methods for automatically inspecting various aspects of railway rolling stock are advantageous for a number of reasons. These reasons include allowing the inspection stations to be located at points where most rolling stock is likely to be inspected at reasonable intervals, such as the entrances or exits to rail yards, without having to involve railroad personnel in the actual inspection. Furthermore, such systems and methods are designed to inspect the rolling stock at speed. That is, the inspection occurs while the rolling stock moves at its normal rate of travel past the inspection station. In contrast, manual inspections typically require the rolling stock to be stopped to allow the railway personnel access to the various components to make the measurements. By allowing the rolling stock to move at speed through the inspection station, the inspection can occur without otherwise negatively affecting the schedule of a particular train, thus reducing the cost of the inspection and unnecessary delays in transporting goods along the railway.

However, one disadvantage of inspecting railway rolling stock at speeds is the loss of precision that occurs when taking such measurements of moving railway rolling stock. That is, as railway rolling stock moves along railway tracks, especially at high speeds, the rails and components of the rolling stock move over very complex paths. For example, the weights of the railway rolling stock, which includes both locomotives, freight cars of various types, and passenger cars itself vary considerably. Additionally, the weight distributions of the loads in the railway rolling stock can vary considerably even within one type of rolling stock. As a result, the rails deflect relative to a fixed point on the ground in unpredictable ways, at unpredictable rates, over unpredictable distances based on which kind of rolling stock is passing over that point, and on how that rolling stock is loaded. Similarly, the wheels of the trucks of the railways rolling stock move dynamically relative to the rails in very complex manners. Additionally, the entire piece of rolling stock typically sways and otherwise dynamically moves relative to the trucks and/or the rails as the rolling stock moves along the railway track.

Because all of these weight effects and motions typically occur simultaneously, and thus are superimposed on each other, it becomes difficult, if not impossible, to know the exact position of the rail relative to the ground, the wheel or the car body, the position of the wheel relative to the rail, the ground, or the car body, or the car body relative to the wheel, the rail or ground using conventional systems and methods. Thus, many of the conventional systems and methods for determining or measuring rolling stock parameters, such as those outlined above, must accept limitations on the accuracy and/or precision of the measurements can be made.

The inventors have discovered that, especially when working with 2-dimensional images of various components of railway rolling stock, such limits on the accuracy and/or precision limit the usefulness of the obtained images.

This invention provides systems and methods for improving the measurement accuracy of parameters obtained from 2-dimensional images of rolling stock components.

This invention separately provides systems and methods for obtaining improved accuracy and/or precision spatial measurements of rolling stock components.

This invention separately provides reference markers for non-spatial parameters of rolling stock components.

This invention separately provides systems and methods for compensating and/or accounting for unknown relative motions between components of rolling stock and/or railway track components between two images.

This invention separately provides systems and methods for obtaining two or more images containing elements having known spatial relationships.

This invention separately provides systems and methods for obtaining 2-dimensional images of railway rolling stock having elements that indicate relative or absolute positions of objects in the images.

This invention separately provides systems and methods for aligning two or more 2-dimensional images of the same rolling stock component.

This invention separately provides reference markers for locating rail and/or rolling stock components in 2-dimensional images of such rail and/or rolling stock components.

This invention separately provides reference markers attached to rails of railroad track useable to locate objects within an image at high precision and or accuracy.

This invention separately provides reference markers that allow objects within 2-dimensional images of railway components and/or railway rolling stock components to be located at high precision and/or accuracy relative to a fixed point on the ground.

This invention separately provides reference markers for spatial and non-spatial parameters.

This invention separately provides reference markers for measuring thermal parameters of rolling stock components.

This invention separately provides systems and methods for obtaining improved accuracy and/or precision measurements of non-spatial parameters of rolling stock components.

This invention separately provides systems and methods for obtaining both improved accuracy and/or precision measurements of both spatial and non-spatial parameters of rolling stock components.

This invention separately provides a single reference marker that is useable to obtain improved accuracy and/or precision measurements of both spatial and non-spatial parameters.

In various exemplary embodiments, reference markers according to this invention can be attached to rails and/or other dynamically moving components of railroad tracks. In various exemplary embodiments, when images of railway rolling stock are obtained, such that the reference marker(s) appear in the image, measurements of various aspects and parameters of various components of the railway rolling stock can be obtained at high precision and/or accuracy relative to the railroad track component to which the reference marker is attached. Likewise, in various exemplary embodiments, such reference markers allow two such images, obtained at some time interval, to be accurately and precisely aligned relative to the reference marker(s) regardless of the dynamic motion of the railroad track component that occurred at the time the images were captured.

In various exemplary embodiments of reference markers according to this invention, a reference marker, including two or more linked reference markers, can be attached to a relatively stationary structure, such as being staked into the ground. In various exemplary embodiments, the stationary reference marker(s) allows images containing the reference marker to be analyzed to identify parameters and other aspects of the railway rolling stock at high accuracy and/or precision relative to the fixed marker.

In various exemplary embodiments of reference markers according to this invention, the reference markers include optical indicia. The optical indicia allow accurate and/or precise measurements to be taken relative to known points on the reference marker. In various exemplary embodiments, the reference markers allow two images that each contain at least one common reference marker to be aligned relative to the reference marker in the two images. In various exemplary embodiments, the reference markers themselves and/or the indicia have known dimensions and/or have known distances from an image capture device. This allows the reference markers themselves and/or the indicia to act as scales within the images that allow the dimensions of various components, features and/or the like to be determined with high accuracy and/or precision.

In various exemplary embodiments of systems and methods according to this invention, an image containing one or more reference markers is obtained. The image may be analyzed to identify objects of interest in the image and to locate the positions of the one or more reference markers and/or the positions of one or more indicia carried by the reference markers. Once the reference markers and/or the indicia are located, in various exemplary embodiments, the obtained image can be compared or superimposed with other images containing the reference markers and/or the indicia to allow inter-image parameters to be determined, to compare parameter values between the two images, or the like. In various exemplary embodiments, the distance and/or relative position of objects of interest can be determined relative to the one or more reference markers and/or indicia.

In various exemplary embodiments, the indicia can indicate non-spatial information in addition to, or in place of, spatial information. Such non-spatial information can include a reference temperature. In various exemplary embodiments, the reference markers and/or indicia can provide spatial location reference points. In various other exemplary embodiments, the reference markers can provide reference temperature values and/or other non-spatial reference information in addition to, or in place of, the reference position values.

These and other features and advantages of various exemplary embodiments of systems, methods and devices according to this invention are described in, or are apparent from, the following detailed description of various exemplary embodiments of systems, methods and devices according to this invention.

BRIEF DESCRIPTION OF DRAWINGS

Various exemplary embodiments of systems, methods and devices according to this invention will be described in detail, with reference to the following figures, wherein.

Figure 1:
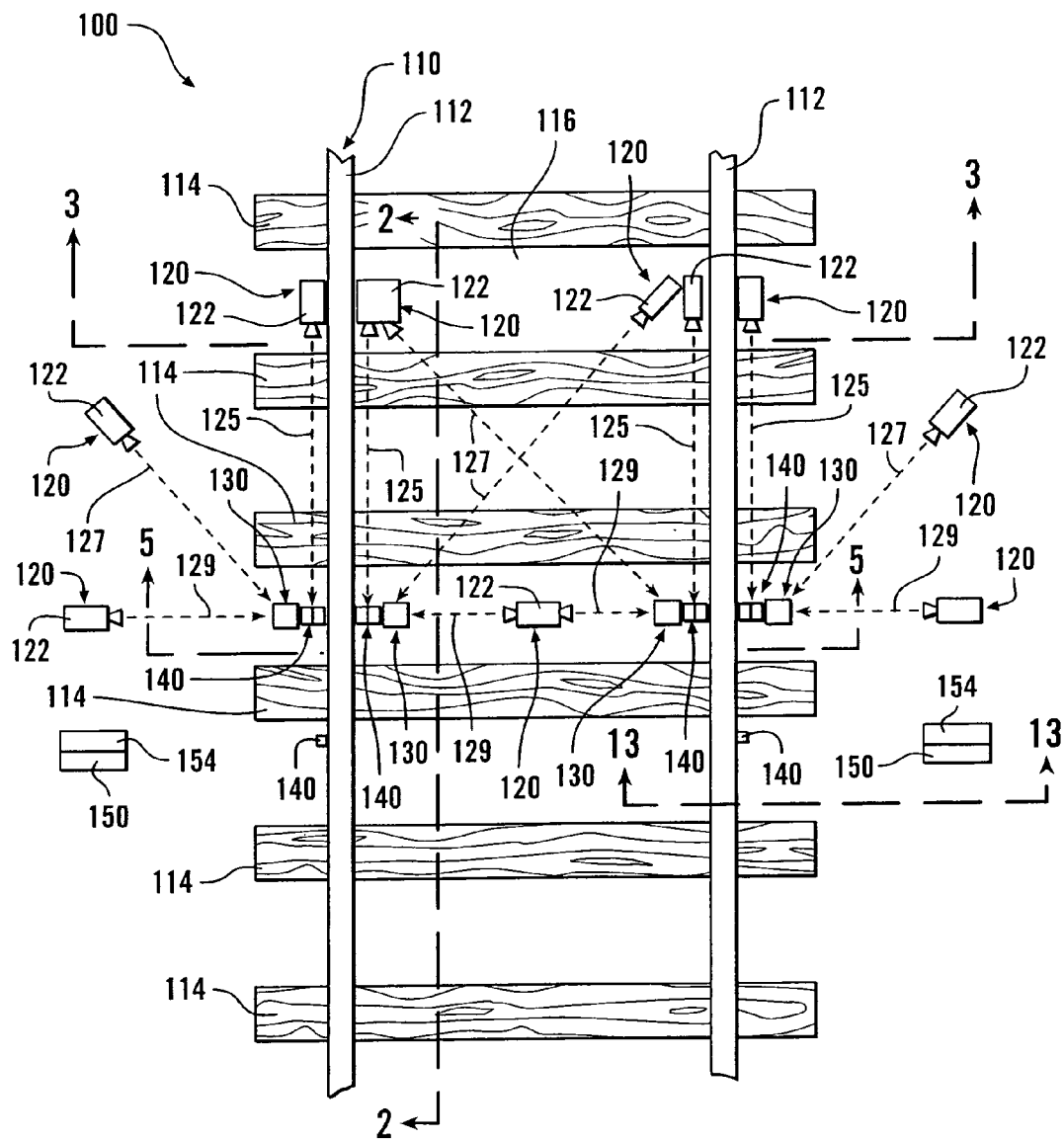
FIG. 1 is a top view of one exemplary embodiment of a section of railroad track having a number of reference markers located on or relative to various components of the railway track.

It should be understood that the drawings are not necessarily to scale. In certain instances, details that are not necessary for understanding of the invention or render other details difficult to perceive may have been omitted. It should be understood, of course, the invention is not necessarily limited to the particular embodiments illustrated herein.

DETAILED DESCRIPTION OF DISCLOSED EMBODIMENTS

A railroad can own tens of thousands, if not more, of pieces of rolling stock. Such rolling stock includes both locomotives and freight and/or passenger cars. Typically, a railroad owns dozens of different types of freight cars, such as box cars, tanker cars, gondolas, hoppers, flat cars, piggy-back flat cars, container carriers, livestock cars and the like. If a railway provides passenger service, the rolling stock can contain passenger cars, baggage cars, mail cars, sleeper cars, dining cars, observation cars and the like. Inspecting rolling stock is typically problematic due to its mobile nature. Accordingly, as outlined in the above-incorporated U.S. patents, automatically inspecting rolling stock as it passes by an inspection station can be significantly more efficient than manually inspecting the rolling stock.

As outlined above, while manually inspecting the rolling stock can give very precise and accurate measurement of various parameters associated with the rolling stock, obtaining such manual measurements is time consuming and expensive. Not only does manual inspection require trained personnel, manual inspection requires stopping a train containing the rolling stock for a period of time sufficient to perform the manual inspection. Because railways earn profits by moving goods from one place to another, delays for inspecting the rolling stock can directly reduce the profits earned by the railway.

Accordingly, as discussed in the above-incorporated U.S. patents, various 1-dimensional sensors have been used to automatically measure various component parameters of rolling stock, especially parameters associated with components of trucks and wheels. Such sensors output 1-dimensional time-varying signals generated as the rolling stock passes by the sensor location. Such 1-dimensional signals represent the measurement taken of the truck and/or wheel as the truck and/or wheel passes by the sensor. It should be appreciated that, even with such 1-dimensional sensors, the accuracy and precision of the measurement strongly depends on the spatial relationship between the sensor and the component being sensed.

More recently, as machine vision and image processing capabilities have improved, such 1-dimensional sensors have been replaced or augmented with optical, infrared and other 2-dimensional sensors that are able to produce 2-dimensional images. Such 2-dimensional images can include optical images, obtained using a CCD array, a digital still or video camera, or any other known or later-developed device for capturing and storing optical image data. Such 2-dimensional image data can also include infrared or thermal image data obtained using an infrared camera, an infrared CCD array or any other known or later-developed infrared or thermal image capture device. Such infrared or thermal images provide information about the temperature of the components being imaged.

Due to recent improvements in image capture technology and automated image analysis, it is possible to use such 2-dimensional images of components of rolling stock to generate highly precise and highly accurate measurements of such components and parameters for the rolling stock. However, such highly precise and/or highly accurate measurements typically require that the image processing systems and methods be able to accurately, precisely and correctly identify objects appearing in the captures images and their spatial locations both within the images and relative to some fixed and/or known location. Systems, methods and devices according to this invention are useable to improve the accuracy and or precision of such 2-dimensional images and 1-dimensional images.

Automatic inspection of rolling stock also permits the railways to operate the trains at speed through the inspection stations, due to the ability of image capture devices to capture images of the rolling stock over very short exposure times that avoid any blurring or movement of the components within the captured image. Thus, it becomes possible for the railways to avoid having to stop, or even substantially slow, the trains to allow the rolling stock to be inspected. Because the trains do not need to significantly alter their current speed when moving through the inspection stations, the trains can be operated individually at the speeds most efficient for their particular cargos and destinations.

As indicated above, freight cars can have widely differing weights based on, among other things, the particular type of freight car, its cargo, and its load. As a result, components of the rolling stock, such as the trucks, the wheels, the springs and the like, as well as the different components of the track, such as the rails, sleepers and the like, typically move dynamically over a significant spatial range. These motions can include vertical, horizontal and rotational movements. Thus, a typical rail will experience significant lateral, vertical and twisting movements as the rolling stock moves over it. As indicated above, these lateral, vertical and/or twisting motions arise due to the differing weights of various pieces rolling stock, their differing load distributions and the like. Similarly, a typical piece of rolling stock will sway, lean and the like, while its trucks and wheels move in various ways on the rails.

Because of these motions of both the rail and the rolling stock, it becomes extremely difficult to capture an image of a component of the rolling stock where the component is inherently at a known position, either vertically, horizontally or even rotationally, relative to the image capture device. Furthermore, effects such as hunting, and the like, as disclosed in U.S. Patent Application Ser. No. 60/588,910, which is incorporated herein by reference in its entirety, add further complexities in determining the position of the components in the image. These dynamic motions make it difficult to measure components of a cargo or passenger car or locomotive, and other pieces of rolling stock accurately while in motion.

Parameters that are typically measured or derived using such captured images include dimensions and/or parameters relative to wheel hollowing, wheel flange height, wheel flange width, wheel rim thickness, wheel flange angle, the back-to-back distance of a pair of wheels connected by the same axle, the lateral position of a particular wheel along the rail, axel straightness, end cap center-ness, coupler height, and the like. Such captured images can also be used to determine whether a vehicle is leaning improperly, due to a variety of conditions such as a broken suspension component, e.g., a leaf spring, or even if a vehicle is out of gage.

"Out-of-gage" refers to a situation or condition where a portion of a vehicle extends beyond a boundary and/or outside of an envelope that defines the safe operating space of a rail bed. For example, tunnels, bridges, cliff sides and the like provide fixed hard constraints for how far to each side or above the rail bed a particular piece of rolling stock can extend before it contacts such tunnel, bridge, abutment, cliff face or the like. This envelope can also define the safe operation of one train as it passes by another train or by other elements that are located near the tracks, such as switches, signals, buildings and the like.

If a particular piece of rolling stock is out of gage, the likelihood that the piece of rolling stock will catastrophically contact an adjacent structure or the like increases significantly. Because such catastrophic failure will typically go well beyond mere damage to that piece of rolling stock, and can include train derailment, leakage of hazardous material, especially into a residential area, injury to those onboard the train, especially if the train is a passenger train, and to those in the vicinity of the train when a problem occurs, rolling stock that is out of gage is extremely hazardous and must be dealt with immediately. However, due to the economic costs of stopping a train for a potential out-of-gage situation, verifying such an out-of-gage situation before taking the potentially drastic step of halting the train is highly desirable.

In the following detailed description, the various reference markers 130 and 140 and image capture devices 120 are described as being inside or outside of various elements, such as the rails 112, other ones of the reference markers 130 and/or 140 and the like. In general, the reference markers 140 are between the reference markers 130 and the rail 112, regardless of whether those reference markers 130 and 140 are inside of, that is, between the pair of rails 112 or outside of the rails 112, that is, not between the pair of rails 112. Thus, the reference marker 140 may be described as "next to the rail 112 inside of the reference marker 130," even if both are also described as being "outside of the rails 112."

FIG. 1 shows one exemplary embodiment of an inspection station 100 according to this invention. As shown in FIG. 1, in one exemplary embodiment, the inspection station 100 comprises a section 110 of track where a variety of image capture devices 120 and ground-mounted reference markers 130 and/or rail-mounted reference markers 140 according to this invention are located. As shown in FIG. 1, in one embodiment, the section 110 of track includes portions of a first rail 112 and a second rail 112 that are mounted to a number of sleepers 114. The sleepers 114 may be embedded in a mass of ballast. The rails 112 are connected to the sleepers 114 using any known or later-developed technique and/or device. As shown in FIG. 1, image capture devices 120 may be located outside one or both of the rails 112 and/or between the rails 112.

Locating one or more image capture devices 120 inside of or between the rails 112 allows determination of various measurements, dimensions and/or conditions such as wheel hollowing, back-to-back distance and axel straightness, flange height, flange width, rim thickness, flange angle, lateral position of the wheel on the rail, among other parameters. In particular, determining the back-to-back distance typically requires locating sufficient image capture device(s) 120 so that images of both wheels of the same wheel set are captured with at least one reference marker located in each image. If the distance between a reference marker in one captured image and a reference marker in the second captured image is known, fixed and/or can be determined, the back-to-back distance can be readily determined. Image capture devices 120 located outside of the rails 112 allow parameters such as diameter of the wheel, hollowing (or false flanging) of the rim and the like to be determined.

As depicted in FIG. 1, various ones of the ground-mounted reference markers 130 and/or the rail-mounted reference markers 140 can be located inside of or between the rails 112 and/or outside of the rails 112. As shown in FIGS. 2, 5, 7 and 9, the ground-mounted reference markers 130 may be interconnected to posts 134 or the like that are embedded in and/or through the ballast 116 and/or may be interconnected to each other by a second member, such as a rod, plate or web, a truss assembly or the like. In one embodiment, the rail-mounted reference markers 140 are adapted to be interconnected to the rails 112 or other components of the rail system such as the sleepers 114.

Thus, the rail-mounted reference markers 140 may be used to provide an indication of the spatial position of a wheel relative to the rail 112 but may not define, by themselves, a position of the wheel, or the rail 112, relative to a generally fixed point. In contrast, the ground-mounted reference markers 130 allow locations of various features of the wheels, the rails 112, and the like to be determined relative to a generally fixed point, regardless of any relative motions may have occurred between the wheel and the rail-mounted reference markers 140. Furthermore, when both a ground-mounted reference marker 130 and a rail-mounted reference marker 140 appear in a same captured image, the position of the rail-mounted reference marker 140 relative to the ground-mounted reference marker 130 may be readily determined, providing a second method for determining the position of features on the wheel relative to the ground-mounted reference markers 130.

As illustrated in FIG. 1, in various exemplary embodiments, image capture devices 120 may be positioned in the region between the rails 112, such as between the reference markers 130/140 on a first rail and the reference markers 130/140 on a second rail. As illustrated in FIG. 1, an image capture device 120 can be positioned to view in any direction such as along the rails 112, e.g., along the view lines 125, diagonally across the area between the rails 112, e.g., along the view lines 127, and/or perpendicularly across the area between the rails 112, e.g., along the view lines 129. It should be appreciated that each image capture device 120 can include one or more physically distinct imaging systems. For example, in various exemplary embodiments shown in FIG. 1, the image capture devices 120 can include a single imaging system that points generally along one of the view lines 125, 127 or 129. In various other exemplary embodiments shown in FIG. 1, the image capture devices 120 can include multiple imaging systems that are able to view along multiple view lines.

It should be appreciated that the image capture devices 120 can be implemented by incorporating one or more physically distinct imaging systems, such as complete digital cameras, into an image capture device body 122. In one embodiment, the image capture devices 120 can be implemented as a plurality of physically independent image capture systems, such as complete digital cameras. In one embodiment, the image capture devices 120 can implement one or more imaging systems using physically distinct lens assemblies and image capture electronics, with common data storage, input/output control and other electronics. It should be appreciated that any known or later-developed type or types of image capture systems may be used to implement the image capture devices 120.

While FIG. 1 shows image capture devices 120 located between the rails 112 having two (or more) imaging systems, these image capture devices 120 may have only a single imaging system. Likewise, while FIG. 1 shows image capture devices 120 located outside the rails 112 having a single imaging system, these image capture devices could have two or more imaging systems. One such embodiment is where two adjacent sets of rails 112 each have an inspection station 100 and those inspection stations 100 share the image capture devices located in the area between the two sets of rails.

It should also be appreciated that any particular inspection station 100 does not need to use all of the image capture devices 120 shown in FIG. 1. Nor is any particular inspection station 100 limited to the image capture devices 120 and lines of view 125, 127 and 129 shown in FIG. 1. It should be appreciated that FIG. 1 shows a number of distinct embodiments for image capture devices 120 that are located near one another. In an actual image inspection station 100, any number of embodiments could be used for such image capture devices 120. Other locations and/or lines of view can be used with the image capture devices 120 shown in FIG. 1. Thus, the locations of, and view lines of, the image capture devices 120 shown in FIG. 1 are merely illustrative, and are not intended to be limiting.

Figure 2:
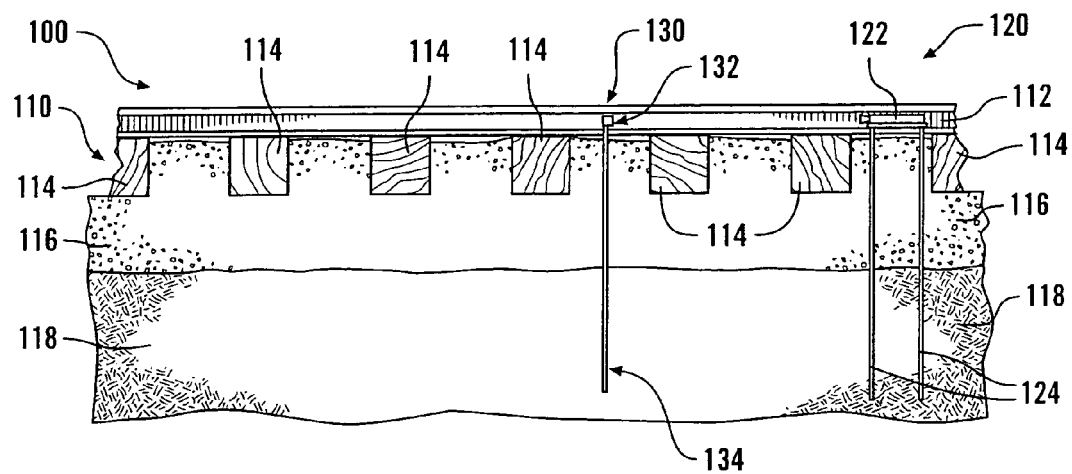
FIG. 2 is a side cross-sectional view along the reference line 2-2 shown in FIG. 1.

As indicated in FIG. 1, FIG. 2 is a side cross-sectional view along the length of the inspection station 100 taken along the line 2-2. As shown in FIG. 2, the rails 112 may sit on a number of sleepers 114 which may be embedded in a mass of ballast 116. The ballast 116 itself typically sits on the ground 118. As shown in FIG. 2, in various exemplary embodiments, the image capture devices 120 comprise an image capture device body 122 that encloses the one or more imaging systems and at least one mounting pole 124 or the like. The mounting poles 124 typically extend through the ballast 116 and into the ground 118, and thus provide a generally fixed and relatively highly stable position for the image capture body 122.

It should be appreciated that, in various other exemplary embodiments, when the image capture device 120 is located adjacent to one of the rails 112, the image capture device body 122 can be interconnected or otherwise attached to the rail 112. In one embodiment, the image capture device 120 may also be interconnected to a sleeper 114. In one embodiment, the image capture device 120 does not need to be adjacent to one of the rails 112, and may be located anywhere along the lateral extent of the sleeper 114, either between the rails 112 or outside of the rails 112.

In those exemplary embodiments where there is at least one ground-mounted reference marker 130 and at least one rail-mounted reference marker 140 in a field of view of an image capture device 120, the captured image will be able to indicate any motion or movement of the rail-mounted reference marker 140 relative to the ground-mounted reference marker 130. When the rail- or sleeper-mounted image capture device 120 moves with the rail, the rail-mounted reference marker 140 will tend to remain within the field of view of that image capture device 120. This will tend to be true even if the image capture device 120 is implemented using a miniaturized or other small-sized image capture system or the like.

Similarly, as shown in FIG. 2, the ground-mounted reference markers 130 include a reference marker head 132 that is, in various exemplary embodiments, attached to a reference marker pole 134. In one embodiment, the reference marker poles 134, when used, may extend through the ballast 116 and into the ground 118, thus providing a generally fixed and a highly dimensionally-stable measuring point for use in measuring components of a piece of rolling stock.

Figure 3:
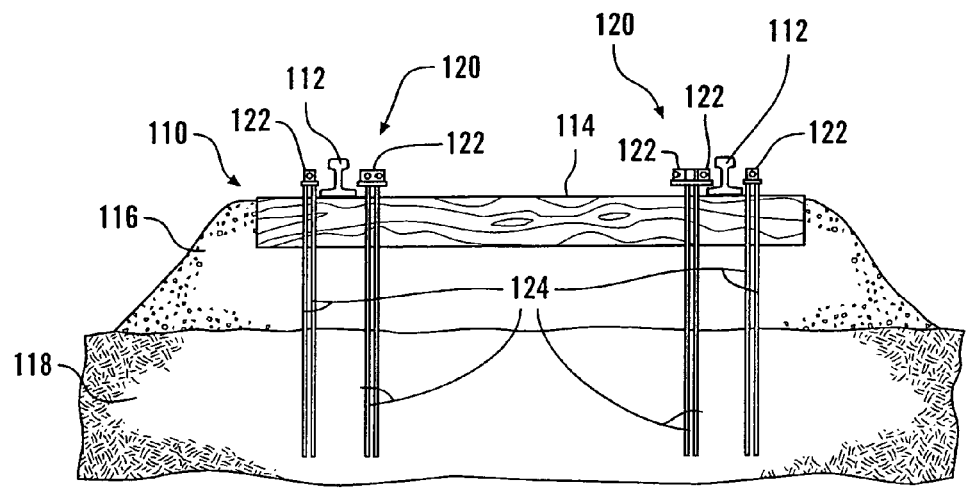
FIG. 3 is a cross-sectional view of the section of railway track shown in FIG. 1, taken along the line 3-3 shown in FIG. 1 showing a first exemplary embodiment of the image capture devices.

As indicated in FIG. 1, FIG. 3 is a cross-sectional view across the width of the inspection station 110 taken along the line 3-3. In the exemplary embodiment shown in FIG. 3, the image capture devices 120 are located between adjacent sleepers 114 and at least just inboard and potentially just outboard of the rails 112 As shown in FIG. 3, in one embodiment, the poles 124 hold the camera bodies 122 securely and/or stably in the ground 118.

It should be appreciated that, in various other exemplary embodiments, the particular location(s) of the image capture devices 120 and/or particular direction(s) of view of the image capture devices 120 for a given inspection station 100 can be altered to any location that is appropriate for the inspection(s) to be preformed at that inspection station 100. It should further be appreciated that any number of image capture devices 120 can be used in a given inspection station 100. Thus, the locations of the image capture devices 120 shown in FIGS. 1-3 are illustrative, and are not intended to be limiting.

It should further be appreciated that the particular locations of the image capture devices 120 shown in the embodiment depicted in FIG. 3 allow any movement of the rails 112 to be readily determined. It should also be appreciated that, in various exemplary embodiments, a wide field of view may be desirable to permit the full motion of the rail 112 to be captured, as well as to improve the ability of the image capture device 120 to capture the reference markers, the rail 112 and its movement, and/or any parts of the rolling stock to be inspected. Thus, in various exemplary embodiments, the image capture devices 120 are arranged so that both the ground-mounted reference markers 130 and the rail-mounted reference markers 140 on a particular side of the rail 112 will be securely within the field of view of the image capture devices 120.

Figure 4:
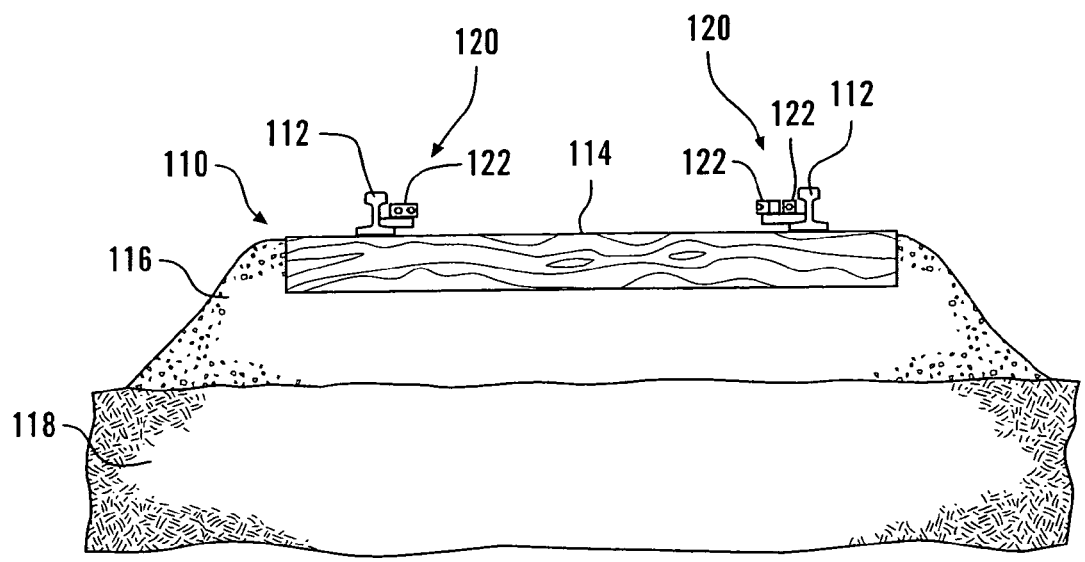
FIG. 4 is a cross-sectional view corresponding to FIG. 3, showing a second exemplary embodiment of the image capture devices.

FIG. 4 shows an exemplary embodiment of the image capture devices 120 located adjacent to the rails 112. As shown in FIG. 4, in this exemplary embodiment, some of the image capture devices 120 are interconnected to the rails 112. Accordingly, in such exemplary embodiments, the image capture devices 120 are able to move with the rails 112. A rail-mounted reference marker may also move with the rail 112. However, in various exemplary embodiments, the image capture devices 120 will tend to capture both the rail-mounted reference markers and the ground-mounted reference marker. It should be appreciated that the rail-mounted image capture devices 120 may be interconnected to the rails 112 using any known or later-developed technique and/or device. In particular, the rail-mounted image capture devices 120 may be interconnected to the rails 112 using the structures shown in the incorporated '910 application.

Figure 5:
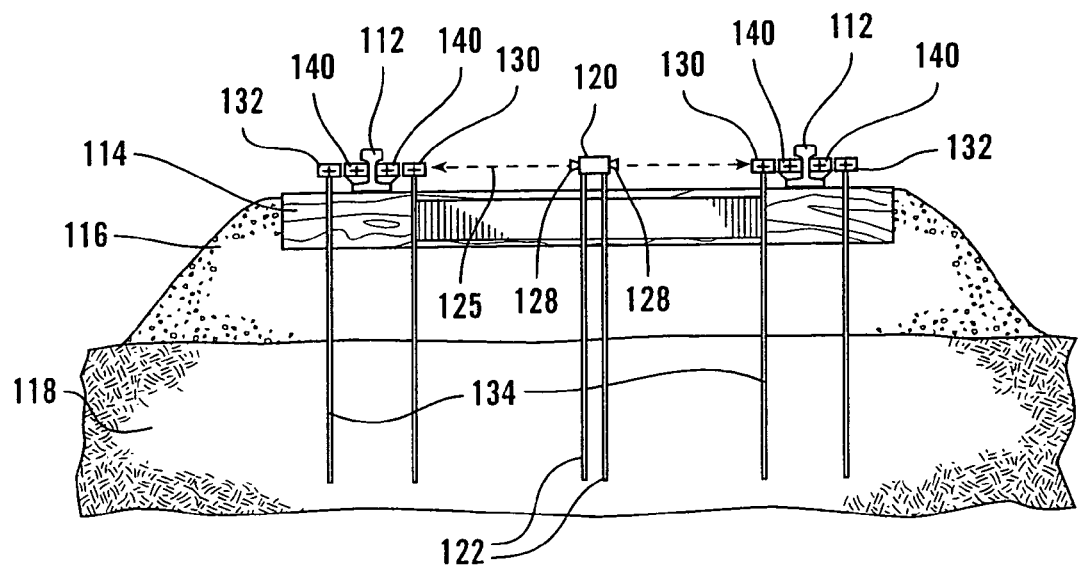
FIG. 5 is a cross-sectional view of another portion of railway track shown in FIG. 1, taken along the line 5-5 shown in FIG. 1 showing a first exemplary embodiment of the reference markers.

Similarly, as indicated in FIG. 1, FIG. 5 is a cross-sectional view across the width of the various reference markers 130 and 140 taken along the line 5-5. As shown in FIG. 5, in one embodiment, the rail-mounted reference markers 140 are connected directly to the rails 112. It should be appreciated that the rail-mounted reference markers 140 can be connected to the rails 112 using any known or later-developed technique and/or device. In particular, the rail-mounted reference markers 140 can be connected to the rails 112 using the structures shown in the incorporated '910 application.

As shown in FIG. 5, in various exemplary embodiments, the ground-mounted reference markers 130 comprise reference marker heads 132 interconnected to poles 134. As shown in FIG. 5, in one embodiment, the poles 134 extend through the ballast 116 and into the solid ground 118. In various exemplary embodiments, at least one second member 138 is interconnected to and extends between the poles 134, the marker heads 132, and/or other portions of the ground-mounted reference markers. In one embodiment, the second member 138 generally rigidly connects the marker heads 132 and/or the poles 134 together such that the relative position of the reference markers 130 and/or reference marker heads 132 remains substantially unchanged. However, the second member 138 does not need to be perfectly rigid. For example, by linking together the ground-mounted reference marker 130 adjacent to a first rail 112 to a ground-mounted reference marker 130 adjacent to a second rail 112, the distance between these opposing ground-mounted reference markers 130 is generally known, making it possible to generate measurements between two parts of rolling stock without having all of the relevant items within a single captured image.

For example, it may be desirable to obtain a measurement extending between a first surface on a first part adjacent to a first rail 112 and a second surface on a second part adjacent to a second rail 112. In this case, separate images may be captured by the image capture devices 120. In one embodiment, one image will include the first surface on the first part, and the ground-mounted reference marker 130 adjacent to the first rail 112. A second image will include the second surface on the second part and the ground-mounted reference marker 130 adjacent to the second rail 112. From these images, the distance from the first and second surfaces to the adjacent ground-mounted reference markers 130 and the distance from the first surface to the second surface may be readily determined.

It should be appreciated that the second member 138 can be implemented as a single element or as a collection of elements, such as a truss. In one embodiment, the single element can be a bar, a plate, a web or the like. In general, any known or later-developed structure, system, device or assembly that is useable to substantially maintain the distance between the ground-mounted reference markers 130 can be used as, or to implement, the second member 138.

Furthermore, in various other exemplary embodiments, the second member 138 can be replaced with a distance-determining device or system that permits the distance between the ground-mounted reference markers 130, the poles 134 and/or the marker heads 132 to be accurately and/or precisely determined at or around the moment the image capture device 120 captures images of the ground-mounted reference markers 130. Examples of such distance-determining devices or systems include a laser range finder or distance measuring device, an ultra-sound distance measuring device, a resistance-based distance measuring device and the like. It should be appreciated that any known or later-developed device that allows a sufficiently accurate and/or precise determination of the position or relative position of the ground-mounted reference markers 130, poles 134 and/or of marker heads 132 to be taken at or near the time the images of the marker heads 132 are captured can be used in place of, or in addition to, the second member 138.

Figure 6:
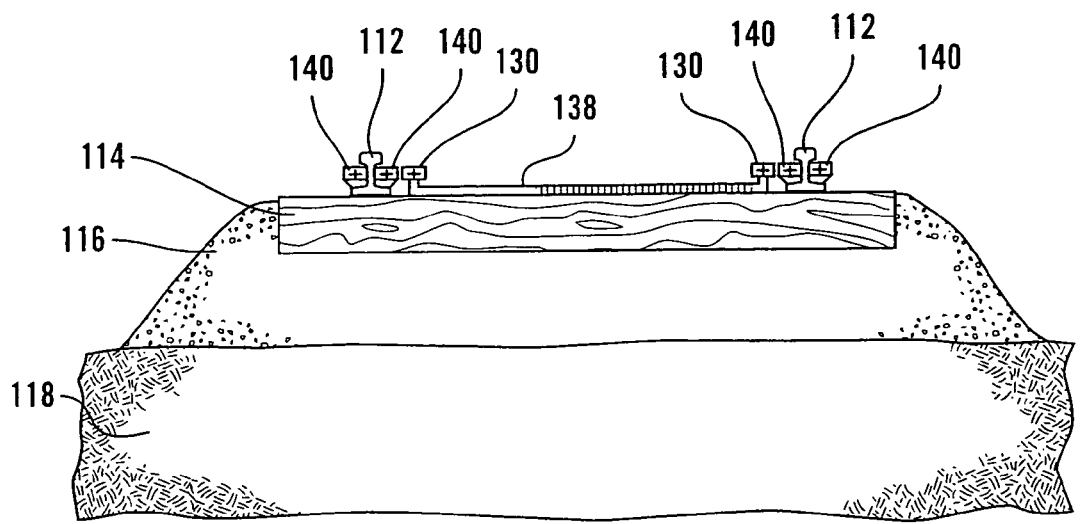
FIG. 6 is a cross-sectional view corresponding to FIG. 5, showing a second exemplary embodiment of the reference markers.

As shown in FIG. 6, in various other exemplary embodiments, the poles can be omitted entirely. In one embodiment, the second member 138 is interconnected to a sleeper 114 or other generally stable structure that is present between the rails 112. In one embodiment, the ground-mounted reference marker heads 132 are interconnected to the second member 138, which in turn is interconnected to the sleeper 114 or similar structure. In one embodiment, the second member 138 maintains the ground-mounted reference marker heads 132 at a substantially fixed and known position and/or distance apart. It should be appreciated that, in one embodiment, additional ground-mounted reference markers 130, such as reference markers interconnected to the sleepers 114, and the like, can also be used. Typically, at least one ground-mounted reference marker 130 and at least one rail-mounted reference marker 140 are arranged so that, for any particular image, at least one ground-mounted reference marker 130 and at least one rail-mounted reference marker 140 appear in the image.

Figure 7:
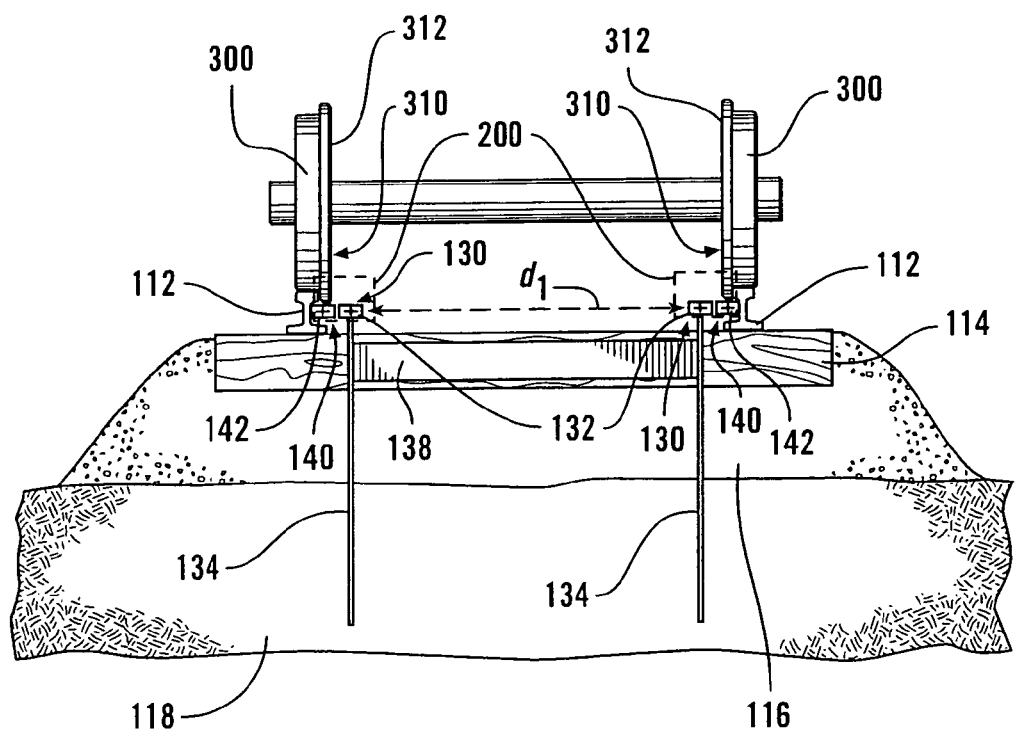
FIG. 7 is cross-sectional view of the section of railway track shown in FIG. 1, taken along the line 5-5, as a wheel of a piece of rolling stock of the railroad passes by the reference markers.

FIG. 7 is a cross-sectional view taken along the line 5-5 shown in FIG. 1, as a truck of a piece of rolling stock passes through the inspection station. In particular, as shown in FIG. 7, a wheel set has at least a pair of opposing wheels 300, where each wheel 300 has a body 310 having a back surface 312. In one embodiment, a first rail-mounted position marker 140 is connected to the side of a first rail 112, a second rail-mounted position marker 140 is connected to the side of a second rail 112, and a pair of ground-mounted reference markers 130 are positioned inside of and/or between the rail-mounted reference markers 140. In one embodiment, the poles 134 and the second member 138 are inserted into the ballast 116 and/or the ground 118 such that the ground-mounted reference marker heads 132 are adjacent to, but between the heads of the rail-mounted reference markers 140, relative to each rail 112. It should be appreciated that, in the exemplary embodiment shown in FIG. 5, the second member 138 allows the distance between the ground-mounted reference marker heads 132 to be known very precisely and/or very accurately.

In various exemplary embodiments, such as those shown in FIGS. 4-7, each of the reference marker heads 132 and 142 contain at least one indicium. In various exemplary embodiments, the indicium has a shape having at least one known dimension. In the particular exemplary embodiments shown in FIGS. 4-6, the indicia formed in or on the reference marker heads 132 and 142 is a "+"-shaped cutout in the reference marker heads 132 and 142. In various embodiments, e.g., if the reference markers 132 and 142 are made out of sheet metal or the like, the indicia formed in the reference marker heads 132 and 142 may be a cutout through the full thickness of the metal.

In various embodiments, e.g., if the reference marker heads 132 and 142 comprise a more substantial piece of metal or the like, the indicia will typically be cut into the surface of the metal. It should be appreciated that the indicium may also be a raised portion left after machining away the other portions of the reference marker. In various other exemplary embodiments, the indicia can be graphic indicia or the like that have been drawn or printed on the reference marker head and/or a decal, a sticker or label, or the like. It should be appreciated that the indicia can be a physical mark worked into the surface of the head of the reference markers 130 and/or 140 and/or can be any known or later-developed surface treatment or the like.

It should also be appreciated that, one embodiment, an indicium can be the marker head 132 or 142 itself or a portion or component thereof. For example, in one embodiment, an edge and/or corner of a marker head 132 or 142 provide acceptable reference points. In addition, the length and height of the marker heads 132 and 142 may provide acceptable scales. In various exemplary embodiments, the marker heads 132 and 142 do not need to contain or carry any other worked-in indicia 136 or 146, respectively.

FIG. 7 also shows the field of view 200 for some of the image capture devices 120 that are arranged, in one embodiment, to view the reference markers 130 and 140 positioned adjacent to the rail 112. As shown in FIG. 7, each field of view 200 may include both the reference marker heads as well as a portion of a wheel 300 and a rail 112. Thus, the position, dimensions and the like of the wheel 300 may be determined relative to the ground-mounted reference marker 130 independently of any movement of the rail 112 relative to the sleeper 114, the ballast 116 and/or the ground 118, as well as any movement of the wheels 300 on the rails 112.

Accordingly, because it is relatively straight-forward to determine the location of various points of the wheels 300 relative to the ground-mounted reference marker heads 130, the ground-mounted reference markers 130 may be used to determine the distance between the back surface 312 of the body 310 of the wheel 300 positioned on a first rail 112 to the back surface 312 of the body 310 of the wheel 300 positioned on a second rail 112. Additionally, the location of the wheel 300 relative to a rail-mounted reference marker 140, and thus to the rail 112, may be used to determine various parameters of the wheel 300 that are defined relative to the surface, e.g., the rail 112, on which the wheel 300 is running. In one embodiment, it is also relatively straight-forward to determine the relative distance between a particular point on the rail-mounted reference marker head 142 and a particular point on the ground-mounted reference marker head 132.

Figure 8:
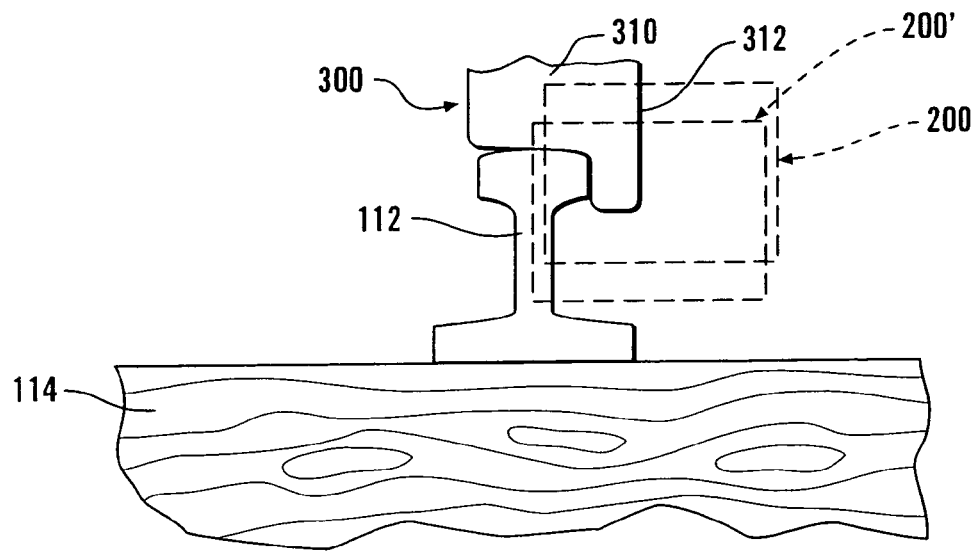
FIG. 8 illustrates inaccuracies that may occur between two images of two wheels taken at different times when no reference markers are present.

FIG. 8 illustrates a situation in one exemplary embodiment when two fields of view or images 200 and 200' are taken in succession. As shown in FIG. 8, in one embodiment, after the first image 200 of the relative position of a first wheel of a truck relative to the rail 112 was captured, the rail 112 bent, twisted, flexed, and/or otherwise moved such that, when the second captured image 200' was taken, the two captured images 200 and 200' do not exactly coincide. Without a reference point, it may be difficult to compare elements in the two pictures.

Figure 9:
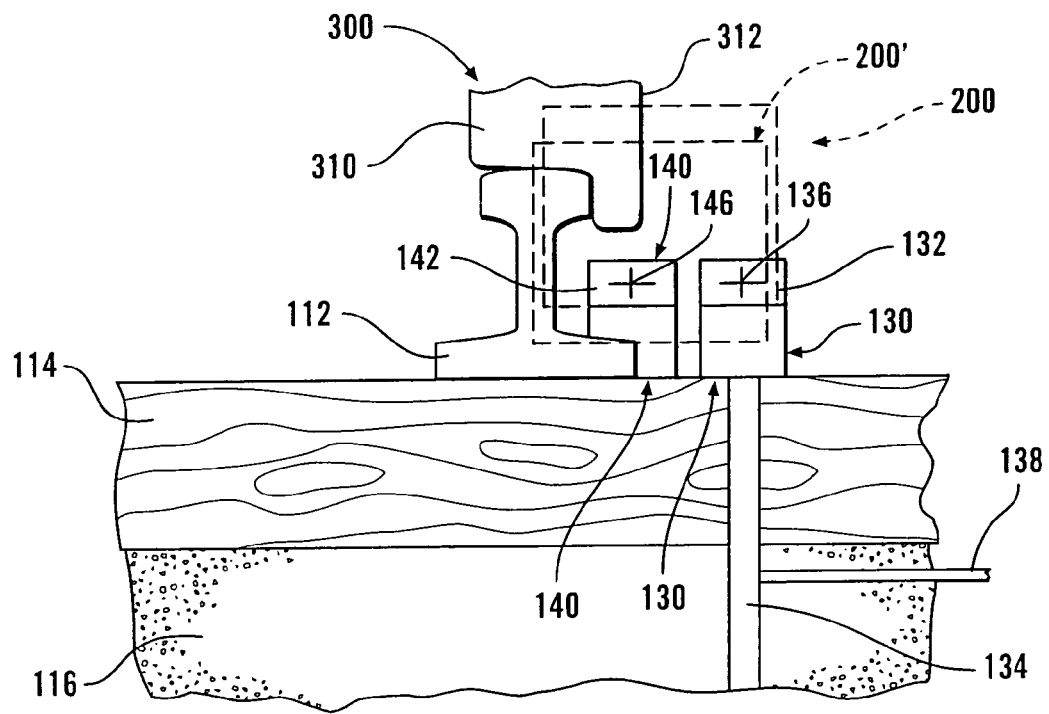
FIG. 9 illustrates two different images taken at two different times of two different wheels using the first exemplary embodiment of the reference markers shown in FIG. 5, where the images also include the reference markers according to this invention.
Figure 10:
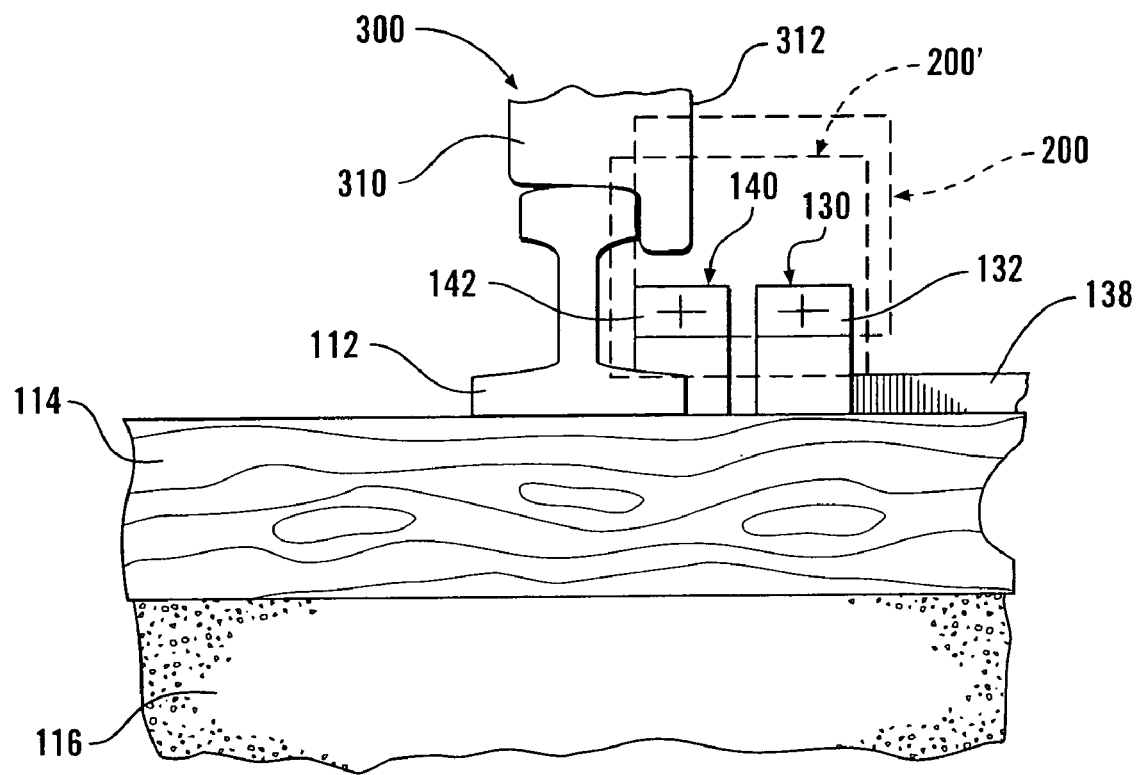
FIG. 10 illustrates the two different images of FIG. 9, using the second exemplary embodiment of the reference markers shown in FIG. 6.

In contrast, in FIGS. 9 and 10, in one exemplary embodiment, the reference marker head 132 and the reference marker head 142, along with the particular spatial indicia 136 and 146, each appear in the two images 200 and 200'. As such, it becomes relatively straight-forward to align or otherwise compare these two images and determine the particular spatial locations of the various objects of interest in each of the two images 200 and 200' relative to a known reference point such as the spatial indicium 136 and/or the spatial indicium 146. Furthermore, because the rail-mounted reference marker 140 is attached to the rail 112 in one embodiment, the indicia 146 allows points on the wheel 310 to be readily located relative to the rail 112.

FIGS. 9 and 10 also show the ground-mounted reference marker heads 132 and second member 138 in one embodiment in greater detail. As shown in FIG. 9, in this exemplary embodiment, the marker head 132 is connected to a pole 134. In one embodiment, the pole 134 is placed into a generally fixed position relative to the ground 118 and extends upwardly through the ballast 116. In one embodiment, the second member 138 extends from the pole 134 toward a second pole that is connected to a second ground-mounted reference marker. In one embodiment, the second member 138 may also extend through the ballast 116. In one embodiment, the second member 138 substantially maintains the two poles 134, and therefore the reference marker heads 132, at a known distance apart. The second member 138 may also prevent the poles 134 from shifting or the like, due to various forces such as stresses applied to the ballast 116 and/or the ground 118 due to the forces applied by a passing train.

FIG. 10 shows in greater detail a second exemplary embodiment of the ground-mounted reference marker 130. As shown in FIG. 10, in this exemplary embodiment, the reference marker 130 is connected to the second member 138. In one embodiment, the second member extends and is operatively connected to a second reference marker. As indicated above, in one embodiment, the second member 138 may be directly connected to the sleeper 114. Of course it should be appreciated that, in one embodiment, the second member 138 may be attached to some other element that is substantially fixed and/or stable relative to the ground, and/or can itself be staked into the ballast 116 or ground 118 using at least one pole 134. In such exemplary embodiments, the distance between the marker heads 132 is substantially fixed and/or constant due to the second member 138, even if the second member 138 should shift relative to the sleeper 114, the ground 118 or other fixed and/or stable element. In one embodiment, the second member may be attached or connected only to at least one ground-mounted reference marker 130 or portion thereof.

Figure 11:
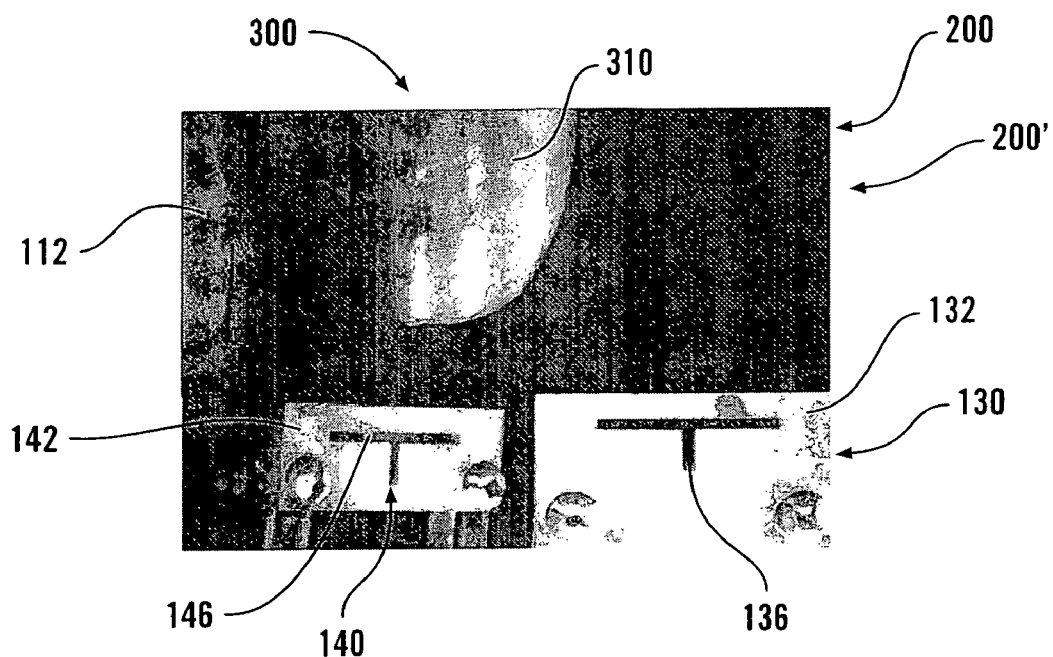
FIG. 11 is a first exemplary captured optical image, showing a wheel of a railway rolling stock, where the image includes reference markers according to this invention.

FIG. 11 is a photograph that, in one embodiment, may correspond to the fields of view 200 and/or 200' shown in FIG. 9 or 10. As shown in FIG. 11, in one embodiment, a ground-mounted reference marker 130, having a reference marker head 132 carrying an indicium 136, is positioned near the rail 112. In one embodiment, rail-mounted reference marker 140, having a reference marker head 142 carrying an indicium 146, is positioned between the rail 112 and the ground mounted reference marker 130. In one embodiment, a In one embodiment, the rail 112 and the bottom portion of the body 310 of the wheel 300 can be seen in the photo of FIG. 11 such that various parameters of the body 310 of the wheel 300 can be measured relative to the rail 112, relative to the ground or some other fixed location, and/or relative to a second wheel 300 on the same axel.

It should further be appreciated that, in various exemplary embodiments, the indicia 136 and 146 have specific, known dimensions, such as thickness of the cut formed in the sheet metal, the length of horizontal crossbar cut and length of vertical crossbar cut. When these dimensions are known, they provide a further calibration factor that allows a conversion between the apparent sizes of the indicia 136 or 146 in the captured image 200 and the actual known sizes of the indicia 136 or 146. Thus, the actual dimensions of objects of interest appearing in the captured images 200, such as the actual width of the flange can be readily determined to high accuracy and precision.

Figure 12:
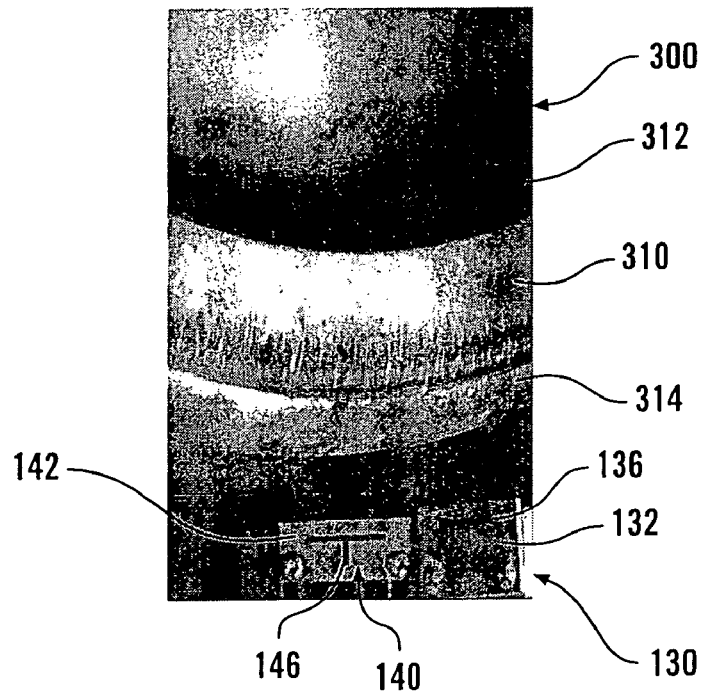
FIG. 12 is a second exemplary captured optical image showing a wheel of a railway rolling stock, showing the back side of the wheel and various exemplary embodiments of reference markers according to this invention.

FIG. 12 is an obtained or captured image of the back face 312 of the body 310 of a wheel 300, captured according to one embodiment of this invention, along with a pair of reference markers 130 and 140 according to one embodiment of this invention. In one embodiment, as can be seen in FIG. 12, the reference marker 130 and 140 need not be positioned along a line lateral to a rail 112. In one embodiment, the reference markers 130 and 140 may be placed along a line following the longitudinal direction of the rail 112. Indeed, the reference markers 130 and 140 may be positioned almost anywhere so long as they are visible by at least one image capture device. For example, the image shown in FIG. 12 was captured using an image capture device positioned between a first rail and a second rail to allow a view of the back surface 312 of the body 310 of the wheel 300 to be obtained and captured, while ensuring that the reference markers 130 and/or 140 remain in the field of view of that image capture device 120.

As shown in FIGS. 11 and 12, in one embodiment, the indicia 136 and 146 on the reference marker head 132 of the ground-mounted reference marker 130 and on the reference marker head 142 of the rail-mounted reference marker 140 are easily seen and their known dimensions can be measured as they appear in the captured image shown in FIG. 12. Accordingly, the dimensions of the body 310 of the wheel 300, such as the width of the rim 314 may also be accurately and/or precisely determined.

Figure 13:
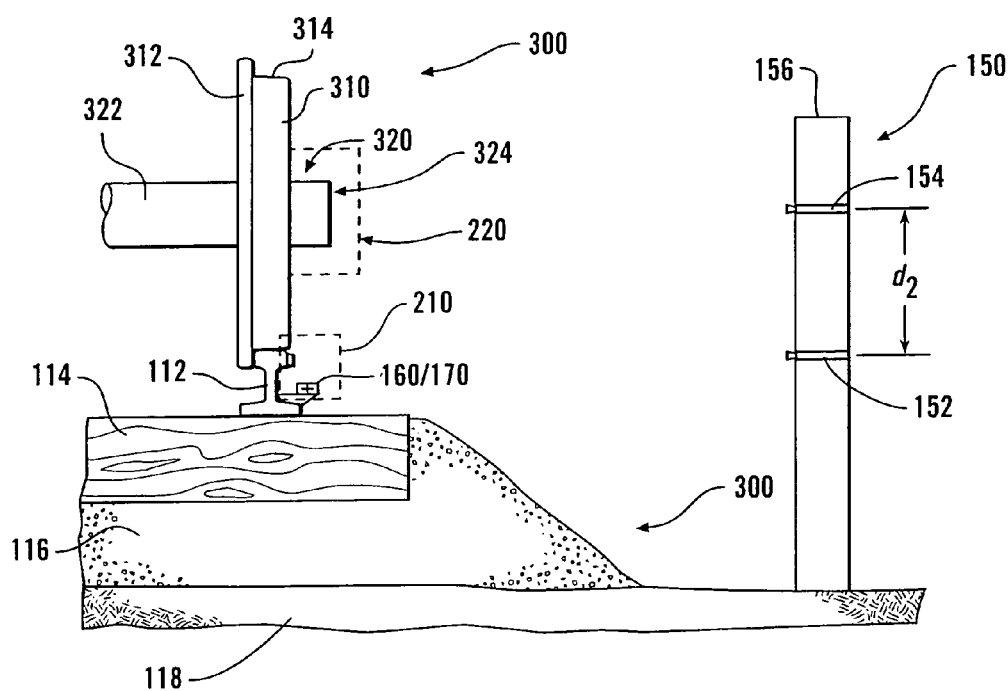
FIG. 13 is a cross-sectional view along the line 13-13 shown in FIG. 1, illustrating a second exemplary embodiment of an image obtaining systems and reference markers according to this invention.

FIG. 13 shows another exemplary embodiment of systems, methods and devices according to this invention. As shown in the embodiment depicted in FIG. 13, a rail 112 is attached to a sleeper 114 that is embedded in a mass of ballast 116 resting on the ground 118. In one embodiment, a mounting structure 150 comprising a post 156 is positioned to the sides of a rail 112. In various exemplary embodiments, the post 156 is substantially dimensionally stable. In one embodiment, a first image capture device 152 and a second image capture device 154 are connected to the post 156 of the mounting structure 150 such that the first image capture device 152 and the second image capture device 154 are at a known and substantially stable distance apart and such that their orientations, and/or the directions of their lines of view are known and substantially stable.

Accordingly, in various exemplary embodiments, the mounting structure 150 and the known and substantially stable relationships of the image capture devices 152 and 154 to the post 156 of the mounting structure 150 allows the two field of views 210 and 220 of the image capture devices 152 and 154 to be related to each other. In one embodiment, a rail-mounted reference marker 160 is attached to the rail 112, such that it is in the field of view 210 of the first image capture device 152. In one embodiment, the image capture device 152 is mounted at a known position on the post 156 of the mounting structure 150 relative to the reference marker 160. In one embodiment, 3-dimensional components, 3-dimensional movement on the rail 112 and/or 3-dimensional images of such components and/or movement may be easily re-created and/or determined using captured 2-dimensional images, information determinable therefrom, and/or relationships of pertinent components of the system of the present invention.

In one embodiment, the reference marker 160 includes an indicium that allows the relative location of the wheel 300 within the field of view 210 of the image capture device 152 to be determined relative to the rail 112. In one embodiment, the indicium also acts as a calibration structure that allows the dimensions within the field of view 210 of the image capture device 152 to be converted to more absolute values. In one embodiment, a temperature reference marker 170 may also be placed within the field of view 210. The front face of this temperature reference marker 170 in one embodiment can be better seen in FIGS. 15 and 17. It should be appreciated that, in various exemplary embodiments, the visual reference marker 160 and the temperature reference marker 170 can be combined into a single component. In one exemplary embodiment, the combined rail-mounted reference marker 160/170 can include both visual and thermal indicia, respectively.

Returning to FIG. 13, in various exemplary embodiments, the second image capture device 154 is located on the mounting structure 150 such that an axel 320 of a wheel set may appear in the field of view 220 of the second image capture device 154. As shown FIG. 13, the wheel body 310 rotates on the axel 320. The wheel 300 includes the wheel body 310 having the flange 316 and the rim 314. The axel 320 comprises a shaft 322 and an end cap 324. In various exemplary embodiments, the second field of view 220 of the second image capture device 154 is centered on the end cap 324.

As indicated in various ones of the incorporated U.S. Patents, various bearings are typically contained in the shaft 322. These bearings can become very hot, especially as they come close to failing. Accordingly, in various exemplary embodiments, the first and second image capture devices 152 and 154 may capture thermal images, in place of, or in addition to, optical images.

Figure 15:
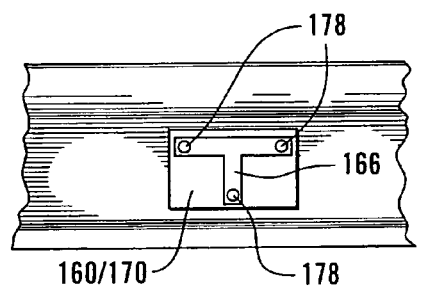
FIG. 15 illustrates another exemplary captured image of a side view of a rail and a related rail-mounted reference marker.
Figure 17:
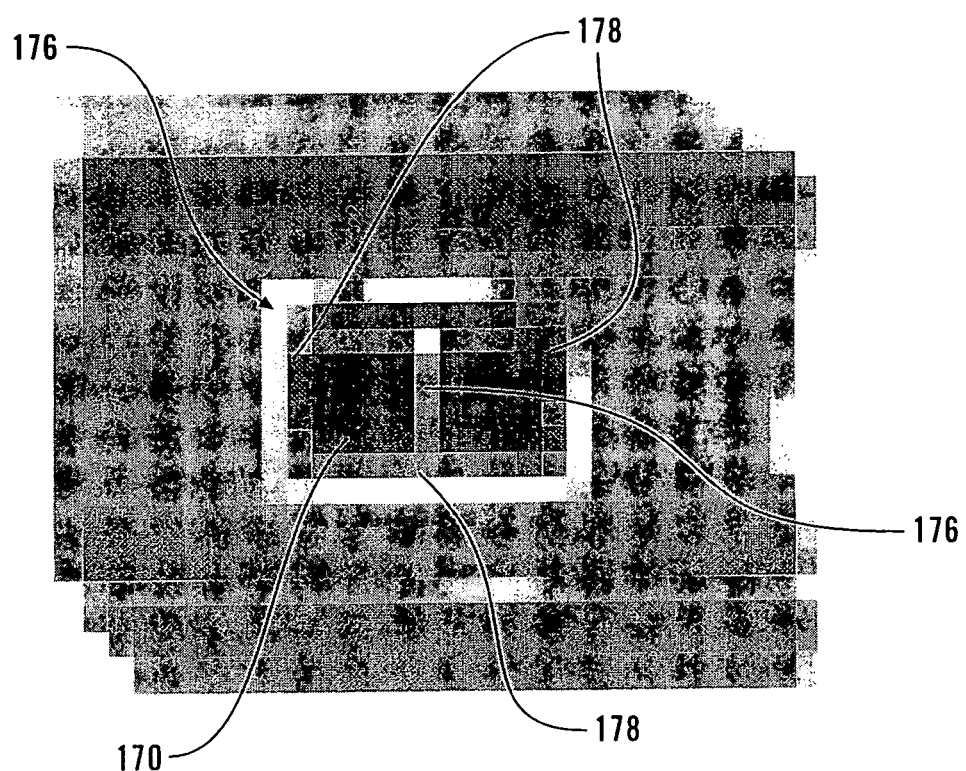

In particular, as shown in FIGS. 15 and 17, when the first image capture device 152 includes a thermal image capture device, the temperature reference marker 170 can include one or more thermally emitting indicia 178. These one or more thermally emitting indicia 178 have at least one known temperature and have known spatial location(s). In various exemplary embodiments, as shown in FIG. 15, the one or more thermal indicia 178 are located at known positions relative to an optical indicium, such as the optical indicium 166, in the rail-mounted reference marker 160/170.

Thus, in one embodiment, while the second image capture device 154 captures one or more images of the end cap 324, the first image capture device 152 captures, at substantially the same time, one or images of the rail 112 and/or the rail-mounted reference marker 160/170. In particular, in one embodiment, the thermal image capture device of the first image capture device 152 captures an image of the thermal reference marker 170 and the one or more thermal indicia 178 that are at the one or more known temperatures. Thus, in one exemplary embodiment, it becomes relatively straight-forward to convert the thermal image data captured by both the image capture devices 152 and 154 into accurate and precise temperature values. In one embodiment, it becomes straightforward to identify the spatial locations of various hot spots, if any, within the end cap 324. Due to the known spatial relationships between the image capture devices 152 and 154 in one embodiment, the spatial locations of these hot spots can be accurately and precisely located relative to the thermal indicia 178 of the rail-mounted reference marker 170.

Figure 14:
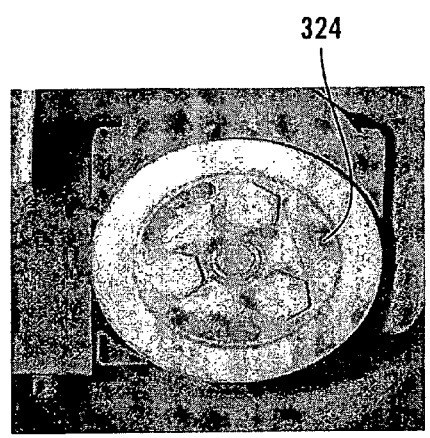
FIG. 14 is a third exemplary captured optical image showing an end cap of a wheel of a railway rolling stock.

FIG. 14 shows one exemplary embodiment of an optical image captured by an image capture device. Because the image capture device is located at a known and substantially stable position and a known and substantially stable orientation in one embodiment, the positions and/or dimensions of various elements of the end cap 324 relative to the image capture device may be determined with high accuracy and high precision.

FIG. 15 depicts one exemplary embodiment of an optical image of the elements that may appear in the field of view of the first image capture device. Images such as those shown in FIGS. 14 and 15 may be captured at generally the same time, though they do not need to be so captured. In one embodiment, the field of view may include both an optical rail-mounted reference marker 160 and a thermal rail-mounted reference marker 170, which, in one embodiment, may be integrated into a combined rail-mounted reference marker 160/170. As shown in FIG. 15, in one embodiment, the combined rail-mounted reference marker 160/170 having both optical indicia 166 and thermal indicia 178 is present within the image captured by the first image capture device.

Because the first image capture device 152 is located at a known position and a known and substantially stable orientation in one embodiment, the positions of the optical and thermal indicia 166 and 178, as well as the surface of the rail, relative to the first image capture device may be determined with high accuracy and/or precision. Because the image capture devices are a known distance apart and are at known relative orientations in one embodiment, the relative locations of the optical indicia 166, and/or the rail 112, among other things, to the elements in the image captured by the second image capture device 154, such as the end cap 324, may be readily determined. In one embodiment, 3-dimensional components, 3-dimensional movement relative to the rail 112, and/or 3-dimensional images of such components and/or movement may be easily determined and/or re-created using captured 2-dimensional images, information determinable therefrom, and/or relationships between pertinent components of the system of the present invention.

Figure 16:
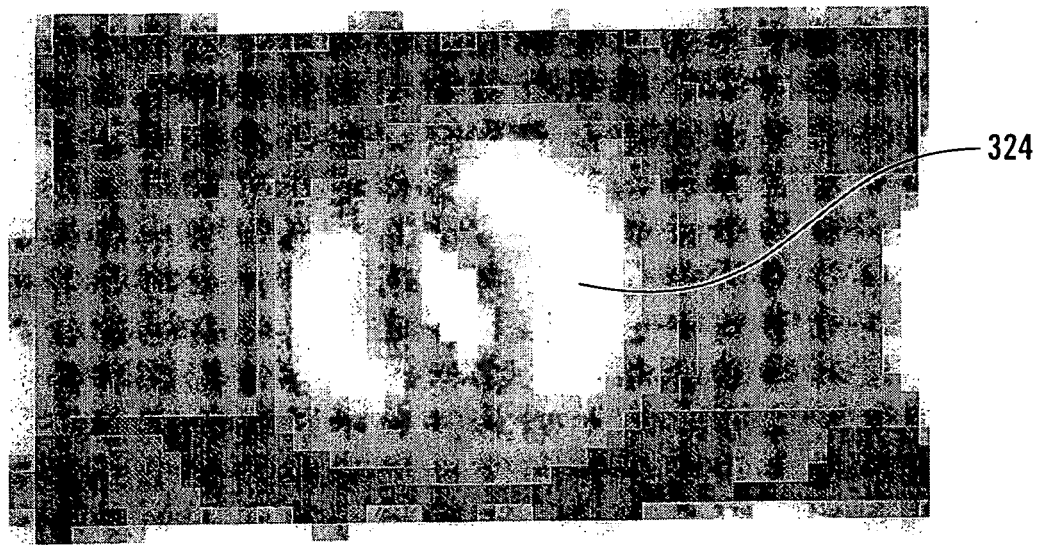
FIGS. 16 and 17 are thermal images of the end cap and reference markers shown in FIGS. 14 and 15.

FIG. 16 is one exemplary embodiment of a thermal image of the end cap 324 obtained using a thermal image capture device. FIG. 17 is one exemplary embodiment of a thermal image of the thermal indicium 178 captured using a thermal image capture device. In one embodiment, the thermal indicia 178 of the reference marker 170 are present in the captured image shown in FIG. 17. In one embodiment, the thermal indicia 178 may be at a plurality of different temperatures and the values in the captured image correspond to these reference temperatures. Thus, the known temperatures of the thermal indicia 178 and the known image values for the thermal indicia 178 allow a calibration curve to be determined for the image data. Thus, the temperatures of the end cap 324 may be determined with high accuracy and precision.

Figure 18:
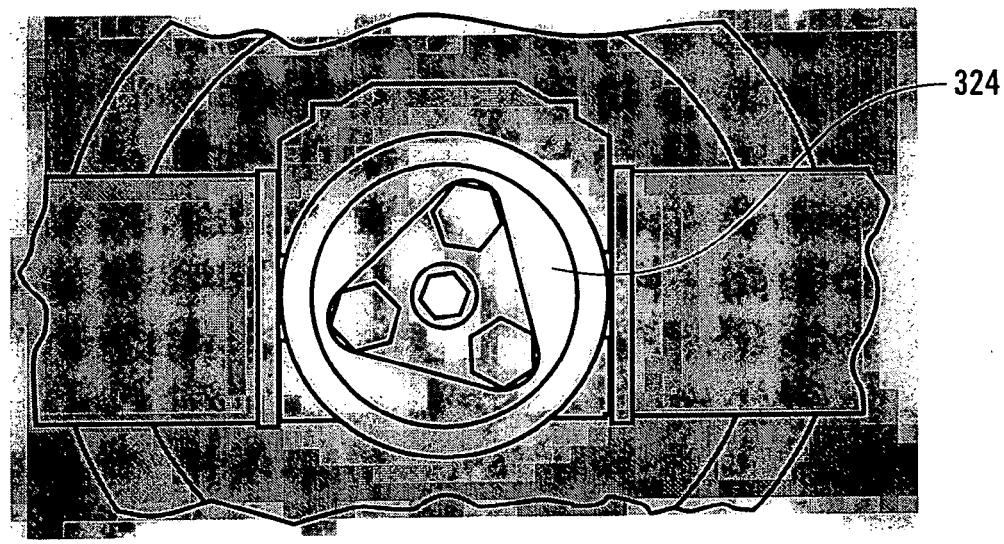
FIG. 18 shows the thermal image of FIG. 16, with a representation of the end cap of FIG. 14 superimposed over it.
Figure 19:
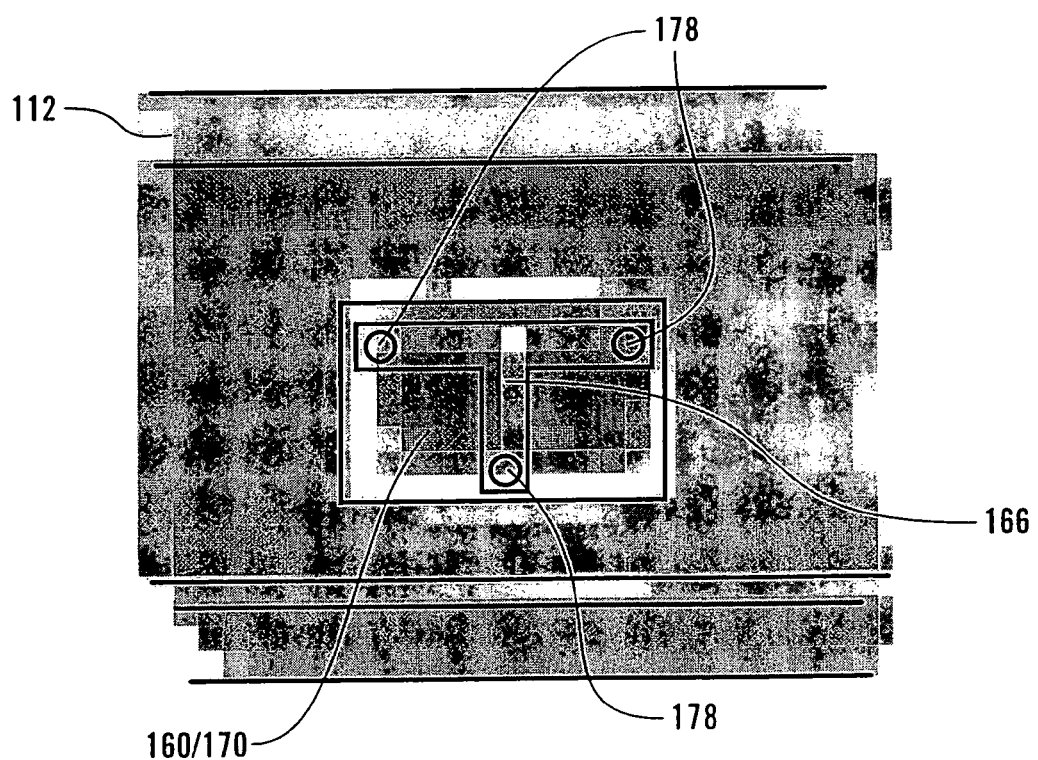
FIG. 19 shows the thermal image of FIG. 15 with a representation of the reference marker superimposed over it.

FIGS. 18 and 19 show the thermal images shown in FIGS. 16 and 17, respectively, overlaid with drawings representing the images shown in FIGS. 14 and 15, respectively. In particular, because the relative position of the thermal indicia 178 visible in the image shown in FIG. 15 is known relative to the optical indicia 166 shown in FIGS. 17 and 19, in one embodiment, the optical image shown in FIG. 15 may be aligned or otherwise compared with the thermal image shown in FIG. 17 as represented in FIG. 19. As shown in FIG. 18, because the relative positions of the thermal image shown in FIG. 16, and the relative positions of the optical images shown in FIG. 14 is known based on the known relative positions and orientations of the image capture devices 152 and 154 in one embodiment, the thermal image shown in FIG. 16 may be aligned or otherwise compared with the optical image shown in FIG. 14. Accordingly, in one embodiment, the positions of the hot spots relative to the end cap 324 may be determined with high accuracy and precision. Furthermore, in one embodiment, if the end cap 324 is not rotationally symmetrical, or comprises a reference mark, the overlaid image not only shows that at least one hot spot exists, but may be used to determine the position of all such hot spots relative to the non-symmetrical end cap 324 or the reference mark on the end cap 324.

Figure 20:
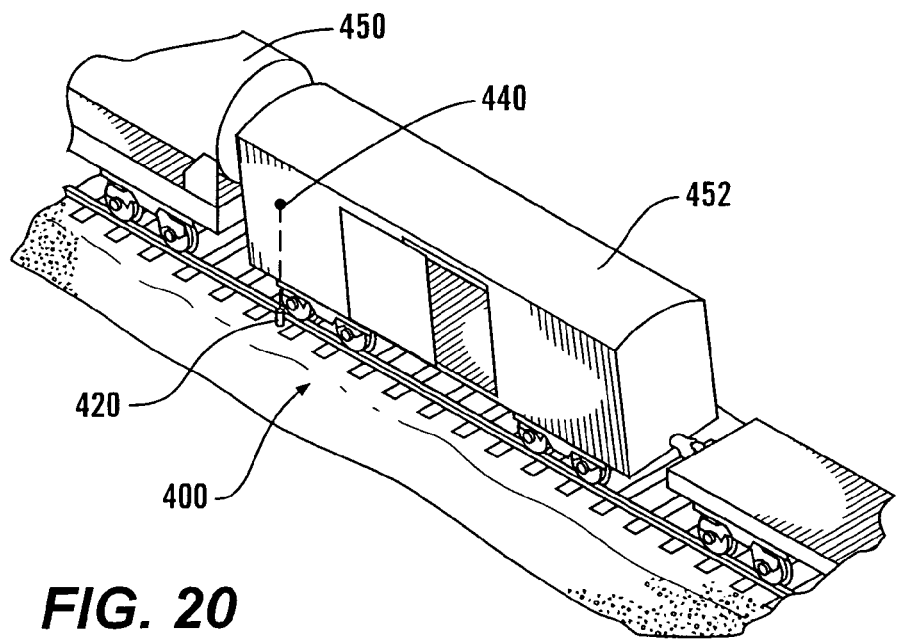
FIG. 20 shows a perspective view of a second exemplary embodiment of an inspection station that incorporates image capture devices and reference markers according to this invention.

FIG. 20 illustrates another embodiment of systems, methods and devices according to this invention. As shown in FIG. 20, a second exemplary inspection station 400 includes, on at least one side of the tracks, at least one vertical image capture device 420 is oriented so that the side of a piece of rolling stock is in a field of view of the image capture device 420. As shown in FIGS. 21-24, in one embodiment, each vertical image capture device 420 captures an image of at least one portion of one side of a piece of rolling stock.

In operation, after the image capture devices 420 have captured two or more images of a piece of rolling stock, the images may be compared or otherwise analyzed. In particular, in various exemplary embodiments, the two captured images from opposite sides of that piece of rolling stock are images captured from opposite ends of the piece of rolling stock. The images are compared to determine if the amount of lean, or an amount of departure from vertical, of the piece of rolling stock is substantially the same in each pair of images. If so, the amount of lean may then be compared to a threshold amount to determine if the amount of lean is beyond a maximum allowable amount. If so, the amount and fixed nature of the lean may indicate a problem with the suspension of at least one of the trucks/bogies of that piece of rolling stock. If desirable, that piece of rolling stock may be withdrawn from service, inspected and, if necessary, repaired, as soon as possible.

It should be appreciated that, as rolling stock moves along railways, the rolling stock having a suspension system in good repair will typically sway back and forth, leaning a small amount in each direction. When at least one suspension component associated with at least one of the trucks has failed in some way, the piece of rolling stock will typically lean an amount that is greater than its designed maximum. Additionally, the piece of rolling stock will typically lean a substantially constant amount, as it can no longer easily sway due to the failed suspension component(s). As such, when the two images of the piece of rolling stock having a suspension system in good repair are taken according to one embodiment of this invention, the amount and/or direction of sway should be different between the two pictures. Indeed, it is unlikely that, when the suspension system is operating correctly, the amount of sway and the direction of sway captured in the two pictures will be exactly identical.

Figure 21:
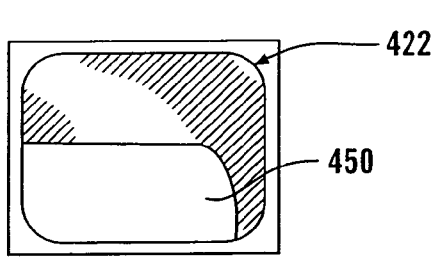
FIG. 21 is a first captured image of a first piece of rolling stock captured using the second exemplary inspection station shown in FIG. 20.
Figure 22:
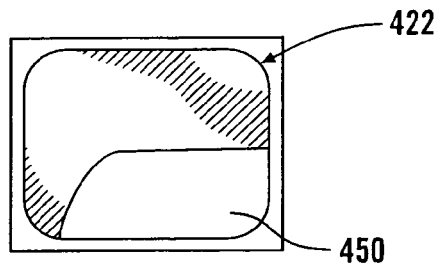
FIG. 22 is a second captured image of the first piece of rolling stock captured using the second exemplary inspection station shown in FIG. 20.
Figure 23:
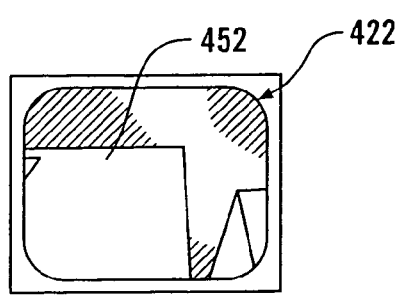
FIG. 23 is a first captured image of a second piece of rolling stock having a broken suspension component captured using the second exemplary inspection station shown in FIG. 20.
Figure 24:
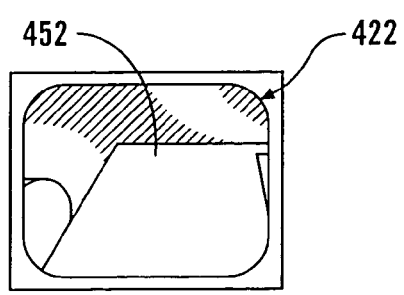
FIG. 24 is a second captured image of the second piece of rolling stock captured using the second exemplary inspection station shown in FIG. 20.

FIGS. 21 and 22 represent captured images, in one embodiment, of the front and rear ends of a tanker car 450 shown in FIG. 20. As shown in FIGS. 21 and 22, the amount and/or direction of lean of the tanker car 450 in these two captured images is different and perhaps below a maximum allowed lean. In contrast, as shown in FIGS. 23 and 24, the piece of rolling stock 452 has, in these two captured images of one embodiment of the present invention; an amount of lean that exceeds the lean limitations and is substantially the same in the two captured images. Thus, the images represented in FIGS. 23 and 24 indicate it is probable that some component of the suspension systems of one or both of the trucks of the rail car 452 have failed and/or are in need of repair. When, in one embodiment, the images of the rail car 452 indicate that the rail car 452 is leaning improperly, the rail car 452 may be withdrawn from service and manually inspected without substantially disrupting the operation of the rest of the train and/or without causing any problem or damage should the suspension system fail further.

Figure 25:
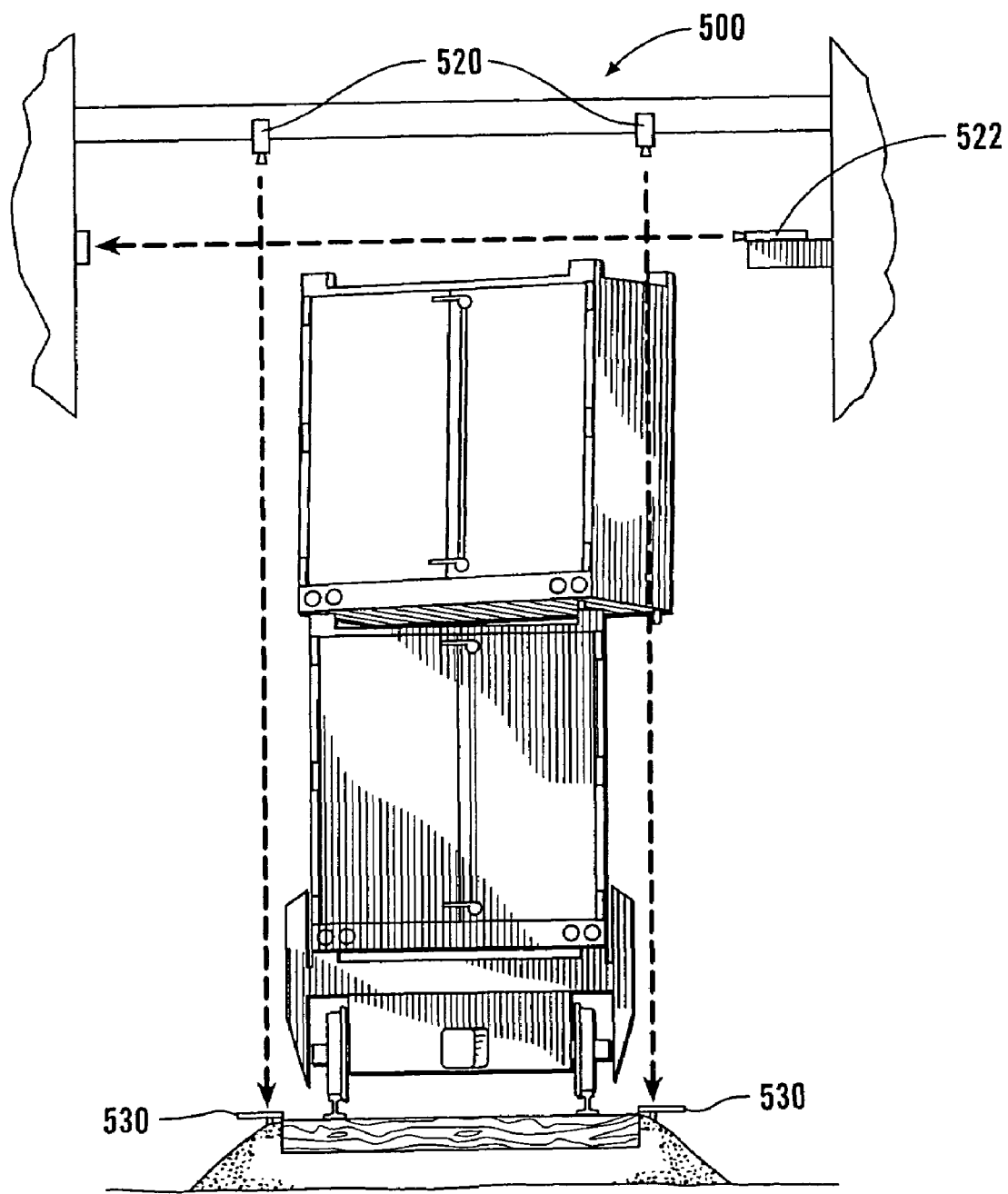
FIG. 25 shows a third exemplary embodiment of an inspection station that incorporates image capture devices and reference markers according to this invention.

FIG. 25 illustrates an out-of-gage situation. In particular, FIG. 25 shows another exemplary embodiment of an inspection station 500 that is useable to determine if a rail car and/or its load is out of gage. As shown in FIG. 25, in one embodiment, the inspection station 500 includes at least one vertical image capture device 520 positioned above and/or to the side of the track and/or the rail car and at least one horizontal image capture device 522 positioned to view across the top of the piece of rolling stock. In various exemplary embodiments, such as those shown in FIG. 25, the vertical image capture devices 520 are connected and/or suspended from an overhanging signal gantry 510 or other structure that extends over the track. In particular, in FIG. 25, the piece of rolling stock is a container carrier. Typically, container carriers are designed to have sea-going cargo containers loaded directly onto them. As shown in FIG. 25, typically, two or more sea-going cargo containers are typically stacked on top of each other on such a piece of rolling stock. While the bottom cargo container can typically be securely attached to the frame of the rail car, it is sometimes more difficult to securely attach the second cargo container onto the first cargo container and/or the third cargo container onto the second cargo container. Accordingly, as depicted in FIG. 25, the second or third cargo container can shift in place on the rolling stock.

In the embodiment shown in FIG. 25, the field of view of the vertical image capture devices 520 and the horizontal image capture devices 522 define an envelope generally corresponding to an out-of-gage envelope of the railroad. In the inspection station 500, in various exemplary embodiments, the image capture devices 520 and 522 are positioned and/or arranged such that the out-of-gage envelope is aligned with a defined point within, the field of view of the image capture devices 520 and 522. As long as a rail vehicle and its cargo stays within the out-of-gage envelope, the rail vehicle and its cargo should not come in contact with any bridges, abutments, sides of tunnels or cliffs, other rail cars, overhangs, signals or the like.

Accordingly, when inspecting rolling stock that is not out-of-gage, no element of the piece of rolling stock or its cargo extends beyond the out-of gage envelope. In contrast, an out-of-gage situation, such as that shown in FIG. 25, will typically have at least one component of the rail car or its cargo extending beyond the out-of-gage envelope.

In particular, in operation, in various exemplary embodiments, as the rolling stock moves past the image inspection station 500, the image capture devices 520 and 522 capture images of the various pieces of rolling stock, or when triggered, such as when a beam extending across the tracks is broken by a wheel or a truck/bogie. Additionally, as set forth above with respect to FIGS. 20-24, due to the dynamic sway nature of the rolling stock, it is necessary to confirm the analysis of the inspection station 500. Further, it should be appreciated, that in various exemplary embodiments, it may be desirable to have portions of the captured images overlap, so that it is clear that no portion of the rolling stock is not viewed or visible in the images obtained by the image capture devices 520 and 522.

As shown in FIG. 25, in one embodiment, at least one reference marker 530, is located at or above rail-level and positioned such that it extends into the field of view of a vertical image capture device 520. It should be appreciated that it may be advantageous to connect the reference marker 530 to the rail so that the contribution of any rail twist, bend or the like can be factored in to the out-of-gage analysis.

In one embodiment, the reference mark may be connected to the ground or another point. Alternatively, the information that can be obtained from the first exemplary embodiment of the inspection station 100 shown in FIG. 1 can be used to provide similar information. That is, as outlined above with respect to FIG. 8, in one embodiment, the amount of rail twist, bend of the like can be identified by comparing the position of the rail-mounted reference marker 140 connected to the rail 112 to the position of the ground-mounted reference marker 130.

In various exemplary embodiments, the reference marker 530 can be a flat plate or sheet-like member that includes a number of spaced-apart lines on the surface facing the image capture device 520 or 522. In general, the lines will run parallel to the rail and/or will be evenly spaced, although they do not need to be. After capturing an image that includes a potentially out-of-gage element and the reference marker 530, the position of the potentially out-of-gage element relative to the gage envelope may be determined. Such a reference marker 530 may also be used to determine the quality of illumination, i.e., how much and how well light is illuminating that reference marker.

Similarly, another exemplary embodiment of an inspection station 500 according to this invention can be used to provide information about the amount of sway of the particular piece of rolling stock when the out-of-gage analysis is performed. It should be appreciated that using the sway and rail bend or twist information when analyzing the particular piece of rolling stock for an out-of-gage situation may be useful to prevent sway and/or rail bent/twist effects from masking what would otherwise be an out-of-gage situation. That is, the direction and amount of rail bend and/or sway may at certain points counteract and otherwise temporarily reduce the severity of a potential and/or intermittent out-of-gage situation. By classifying the amount of rail bend and/or sway based on the reference markers; In one embodiment, a potential out-of-gage situation may be more accurately and precisely analyzed.

In one embodiment, the vertical image capture devices 520 are positioned oriented, and/or arranged such that at least a portion of passing rolling stock will be within a field of view of one or more the image capture devices. In operation, as the rolling stock passes through an image inspection station 500, in one embodiment, the vertical image capture devices 520 capture images of at least portions or components of the rolling stock. In one embodiment, the captured images may also contain one or more reference markers. The captured images may be used to determine the amount, nature and/or extent of lean and/or sway of the rolling stock to determine whether the suspension system of the rolling stock may be in need of repair.

It should be appreciated that, in various exemplary embodiments, at least one image capture device 120, 152, 154, 420, 520 and/or 522 may capture an image at least when one of the trucks of a piece of rolling stock passes by an image capture device. In one embodiment, this may be accomplished by projecting a laser beam or the like at a height above the rails such as a height corresponding to the wheels and/or the trucks or bogies. In one embodiment, a beam may be projected across the tracks, such as between mounting structures located on opposite sides of the track. When the beam is interrupted by the wheel, or by the truck/bogies, in one embodiment, at least one of the image capture devices 120, 152, 154, 420, 520 and/or 522 are triggered to capture an image of the piece of rolling stock. In one embodiment, each time the beam is broken at least one of the image capture devices 120, 152, 154, 420, 520 and/or 522 are triggered. In various other exemplary embodiments, one or more of the image capture devices 120, 152, 154, 420, 520 and/or 522 continually capture images of a piece of rolling stock as that rolling stock passes. In various other exemplary embodiments, a proximity sensor or the like, such as that disclosed in the incorporated '910 application, may be used to provide the trigger signal to one or more of the image capture devices 120, 152, 154, 420, 520 and/or 522. In various embodiments, other known or later-developed apparatus or methods such as mathematical methods may be used to trigger at least one of the image capture devices 120, 152, 154, 420, 520 and/or 522.

In one embodiment, one or more of the image capture devices 120, 152, 154, 420, 520 and/or 522 is associated with a power source and power and signal cables which operably interconnect one or more of the image capture devices 120, 152, 154, 420, 520 and/or 522 with a central processing unit. The central processing unit may include digital signal processors or other devices for storage, transfer, timing and communication of data and/or images from one or more of the image capture devices 120, 152, 154, 420, 520 and/or 522 to the central processing unit. In one embodiment, information from one or more of the image capture devices 120, 152, 154, 420, 520 and/or 522 is communicated to the central processing unit and stored. Communication software and/or data assessment software may be installed on the central processing unit. Communications to the central processing unit may be further processed and/or stored permanently or temporarily on the central processing unit. Communications may also be relayed or transferred to a remote location. The central processing unit may optionally be interconnected to a number of peripheral devices including, without limitation, a visual display unit, a keyboard (or mouse or touch screen), a printer, and/or other suitable peripheral devices for displaying images, data and/or calculations or providing input of commands, signals, etc. The central processing unit, visual display unit and any peripheral devices may be located together or separately at any suitable location or locations and comprising a suitable computer configuration. At least one image capture device 120, 152, 154, 420, 520 and/or 522, the central processing unit, visual display unit, and/or any peripheral devices may communicate by any number of conventional communication paths. For example, but not intended to limit the scope of the invention, communication paths could be a hard wire communication link such as a signal cable and/or a wireless path such as a radio link, cellular path, and/or satellite link.

Figure 26:
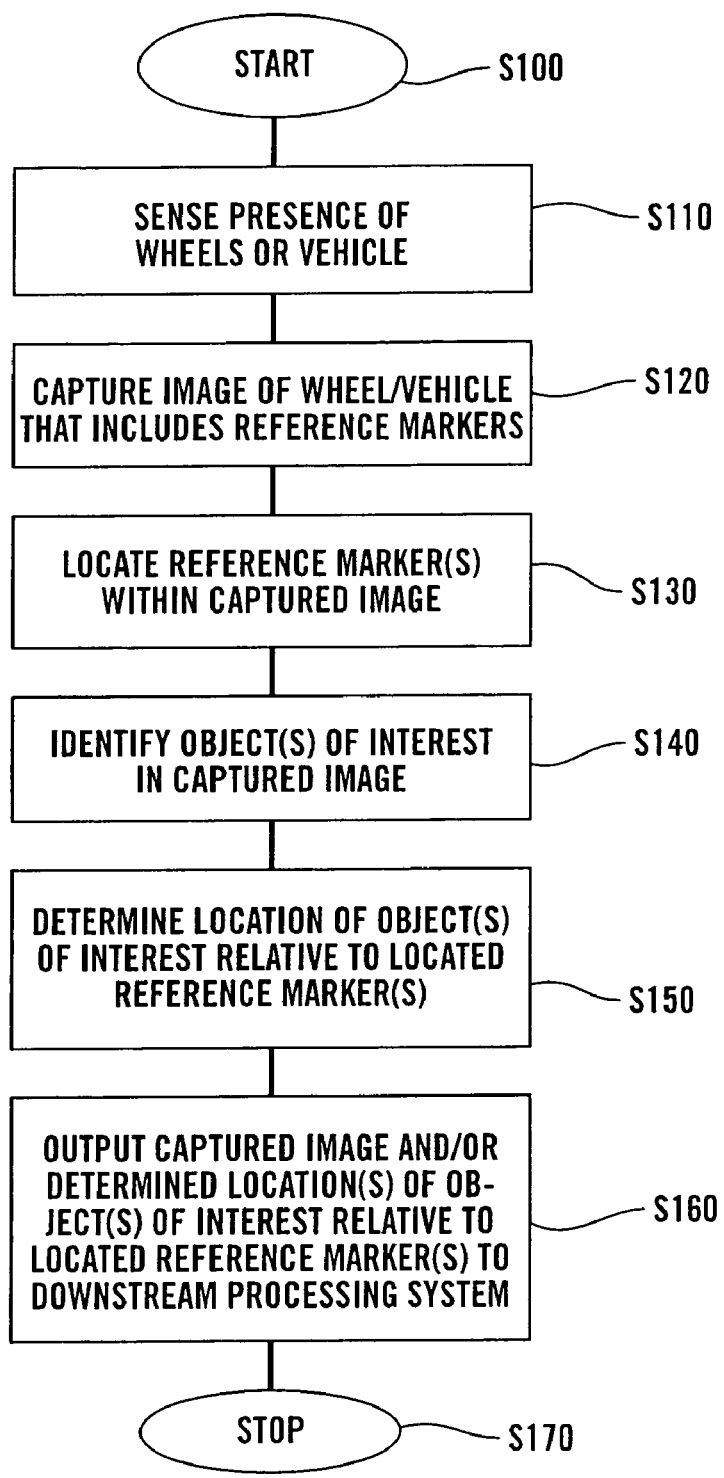
FIG. 26 is a flowchart outlining one exemplary embodiment of a method for obtaining and analyzing images using the reference markers according to this invention.

FIG. 26 is a flowchart outlining one exemplary embodiment of a method for obtaining and analyzing images using reference markers according to this invention. As shown in FIG. 26, beginning in step S100, operation of the method continues to step S110, where the presence of a wheel or other component of a piece of railway rolling stock, or the rail vehicle itself, is sensed. Then, in step S120, an image of the wheel or some other component of interest, where the image includes at least one reference marker, is captured. Next, in step S130, the one or more reference markers within the captured image are located. Operation then continues to step S140.

In step S140, one or more objects of interest that appear, or are supposed to appear, in the captured image are identified. Next, in step S150, the locations of each of the one or more objects of interest are determined relative to the one or more located reference markers. As outlined above, if a particular reference marker appearing in the captured image is a rail-mounted reference marker, the determined location is thus also relative to the rail, or possibly some other particular element, that the rail-mounted reference marker is attached to. As indicated above, that element can be the rail, a sleeper, or any other appropriate element for which the location of the object of interest relative to that element is desired. If a particular reference marker is a ground-mounted reference marker, then the determined location provides a position for the objects of interest relative to the ground or other generally stable element. Then, in step S160, either the captured image, the determined locations of the one or more objects of interest relative to the one or more located reference markers, or both, are output to some downstream processing system or process. Operation then continues to step S170, where the method ends.

It should be appreciated that, in various exemplary embodiments, the downstream processing system or process can be any known or later-developed system, device, method, technique or the like, for further analyzing the captured image and/or the determined location information output in step S160 for each wheel. For example, the downstream processing system or process can combine the relative location distance from the back surface of a wheel of the piece of rolling stock to a ground-mounted reference marker with the known or determined distance between that ground-mounted reference marker and another ground-mounted reference marker in a corresponding image to determine the distance between the back surfaces of the two wheels on the same axel.

Figure 27:
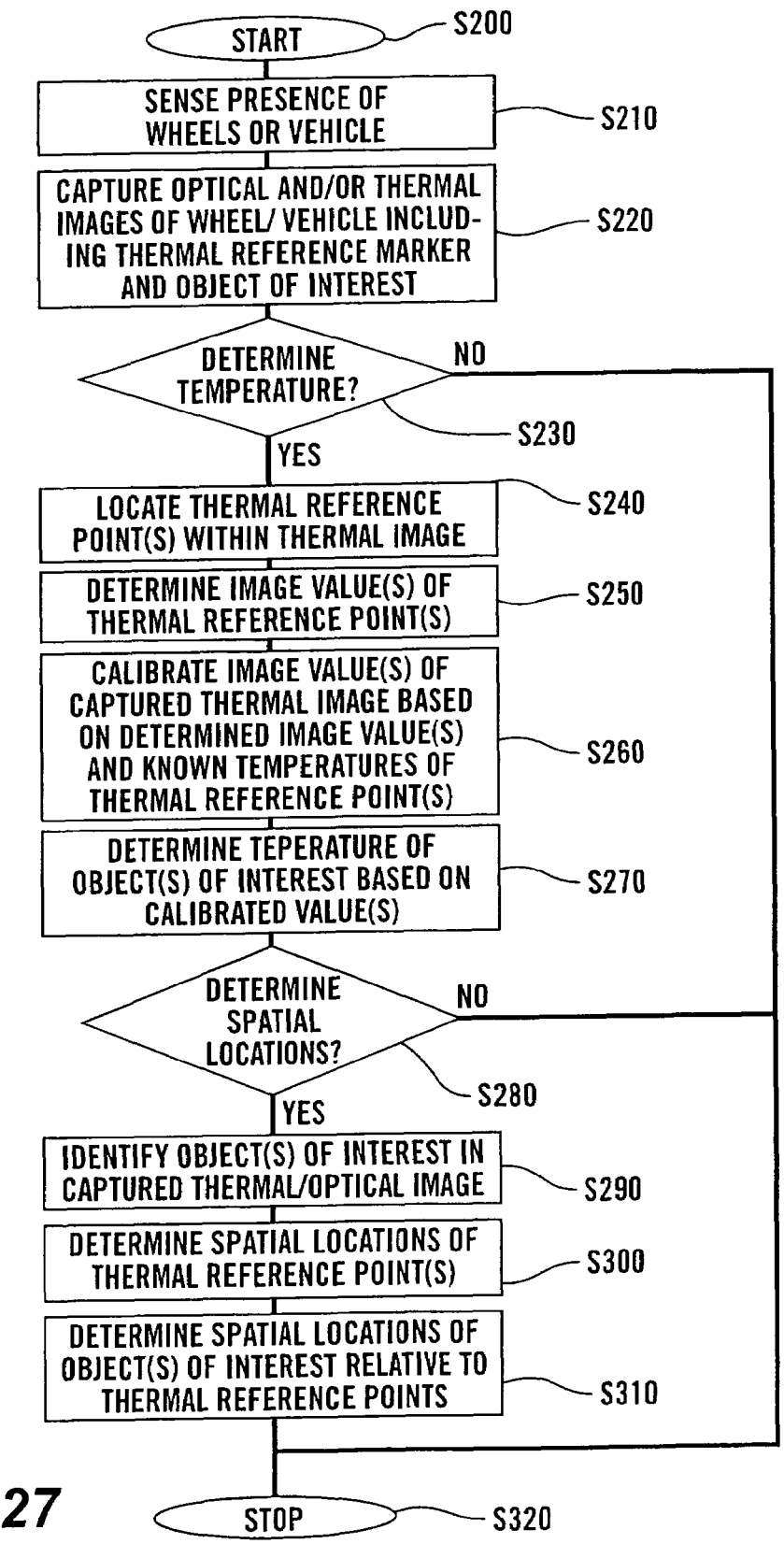
FIG. 27 is a flowchart outlining one exemplary embodiment of a method for analyzing an image using a non-spatial reference marker according to this invention.

FIG. 27 is a flowchart outlining one exemplary embodiment of a method for analyzing and imaging a non-spatial reference marker according to this invention. As shown in FIG. 27, operation of the method begins in step S200, and continues to step S210, where the presence of a wheel or other component of a piece of rolling stock or the rail vehicle itself, is sensed. Then, in step S220, at least one thermal image of the wheel or some other component of interest, is captured and at least one thermal image of a thermal reference marker is captured. The image that includes at least one thermal reference marker will typically be spaced from the image of the wheel or other compound of interest. Next in step S230, a determination is made whether one or more temperature within the captured image is to be determined. If not, operation jumps to step S280. Otherwise, operation continues to step S240.

It should be appreciated that, in various exemplary embodiments, in step S220, in addition to, or in place of, the thermal information, some other type of non-spatial information.

In step S240, one or more thermal reference points provided by the one or more thermal reference markers within the captured thermal reference image are located. Next, in step S250, the image values for the located one or more thermal reference points are determined. That is, if the thermal image is an 8-bit image, such that each pixel within the thermal image has 256 possible values, i.e., values between 0 and 255, the image values of the pixels that correspond to the one or more thermal reference points on the one or more thermal reference markers are determined. Then, in step S260, the image values, such as, for example, image values from 0-255, that occur within the captured thermal image of the component of interest are calibrated based on the determined image values of the thermal reference points and the known temperatures of the thermal reference points. That is, if the thermal reference marker has one, two or even more different reference points having different reference temperatures, a calibration curve can be drawn between the image values for those reference points at different reference temperatures to generate a calibration curve that correlates the image values to various temperatures based on the reference temperatures and the corresponding image values. Operation then continues to step S270.

In step S270, the temperatures of one or more objects of interest that correspond to various areas within the captured thermal image of the component of interest are determined based on their image values in the captured thermal image and the calibration curve determined in step S260. Then, in step S280, a determination is made whether the spatial locations of the objects of interest are to be determined. If not, operation then jumps directly to step S320. Otherwise, operation continues to step S290.

In step S290, the spatial locations of one or more objects of interest are identified in the captured thermal image or a corresponding captured optical image. Next, in step S300, the spatial locations of the thermal reference points within the captured thermal image or within a corresponding captured optical image are determined.

In various exemplary embodiments, the thermal reference points in the thermal reference marker are arranged in a geometric form that is not likely to be present in the captured thermal image. Alternatively, when a corresponding optical image is obtained, the reference markers outlined above with respect to FIGS. 1-8 can be used. In that case, the thermal reference points will typically be located at known positions within the optical reference marker, such as at the ends of the various extending arms, and/or at the intersection of the arms in the reference marker.

Then, in step S310, based on optical or thermal reference points in the thermal reference image or a corresponding captured optical image and known information about the relative locations and/or spatial orientations of the component of interest image capture devices and the reference marker image capture devices, the spatial locations of the objects of interest are located at high precision and accuracy relative to the thermal reference points, to locate the temperatures obtained from the thermal image at high accuracy and precision relative to the components of the piece of rolling stock that appear in the corresponding optical image. Operation then continues to step S320, where operation of the method ends.

Figure 28:
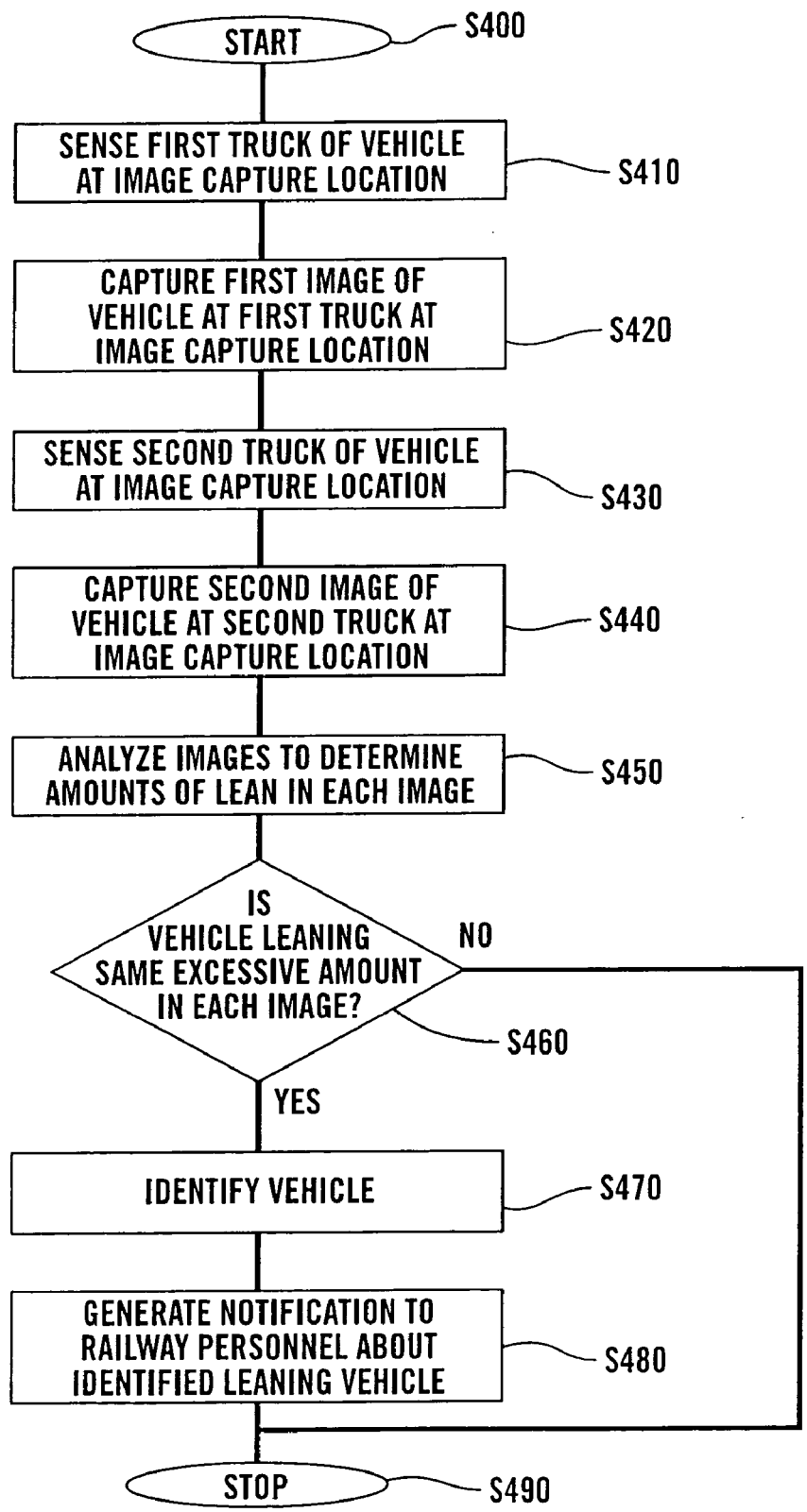
FIG. 28 is a flowchart outlining one exemplary embodiment of a method for determining if a piece of rolling stock is leaning improperly.

FIG. 28 is flowchart outlining one exemplary embodiment of a method for determining if a piece of rolling stock is leaning improperly according to this invention. As shown in FIG. 28, operation of the method begins in step S400, and continues to step S410, where a first truck, or some other designated component, of a piece of rolling stock is sensed as it passes by an image capture location. Then, in step S420, a first image of a piece of rolling stock, as the first truck or the other designated component passes the image capture location, is captured. Next, in step S430, the presence of the second truck, or some other designated component, of the piece of rolling stock as it passes the image capture location is sensed. Operation then continues to step S440.

In step S440, a second image of the piece of rolling stock, as the second truck or the other designated component passes by the image capture location, is captured. Next, in step S450, the first and second images are analyzed, compared or otherwise inspected to determine the amount of lean in each of the first and second captured images. Then, in step S460, a determination is made, based on the analysis, comparison or other inspection, whether the piece of rolling stock is leaning the same amount in each image and whether that amount exceeds a defined threshold. If both situations are found in the captured images, i.e., in both images the piece of rolling stock is leaning by substantially the same excessive amount, operation continues to step S470. Otherwise, operation jumps to step S490.

Because the vehicle is leaning substantially the same excessive amount in each image, and because that amount is greater than the threshold, that piece of rolling stock is leaning improperly, such that it is highly likely that that piece of rolling stock has one or more broken and/or failing suspension components. Accordingly, in step S470, that piece of rolling stock is identified. Then, in step S480, a notification is generated to railway maintenance personnel identifying the particular piece of rolling stock and indicating that it is leaning improperly. In various exemplary embodiments, this notification allows the railway maintenance personnel to pull that piece of rolling stock off the railway and inspect it to determine if any repairs need to be made, and, if so, to make the repairs before the piece of rolling stock fails catastrophically. Operation then continues to step S490, where operation of the method ends.

Figure 29:
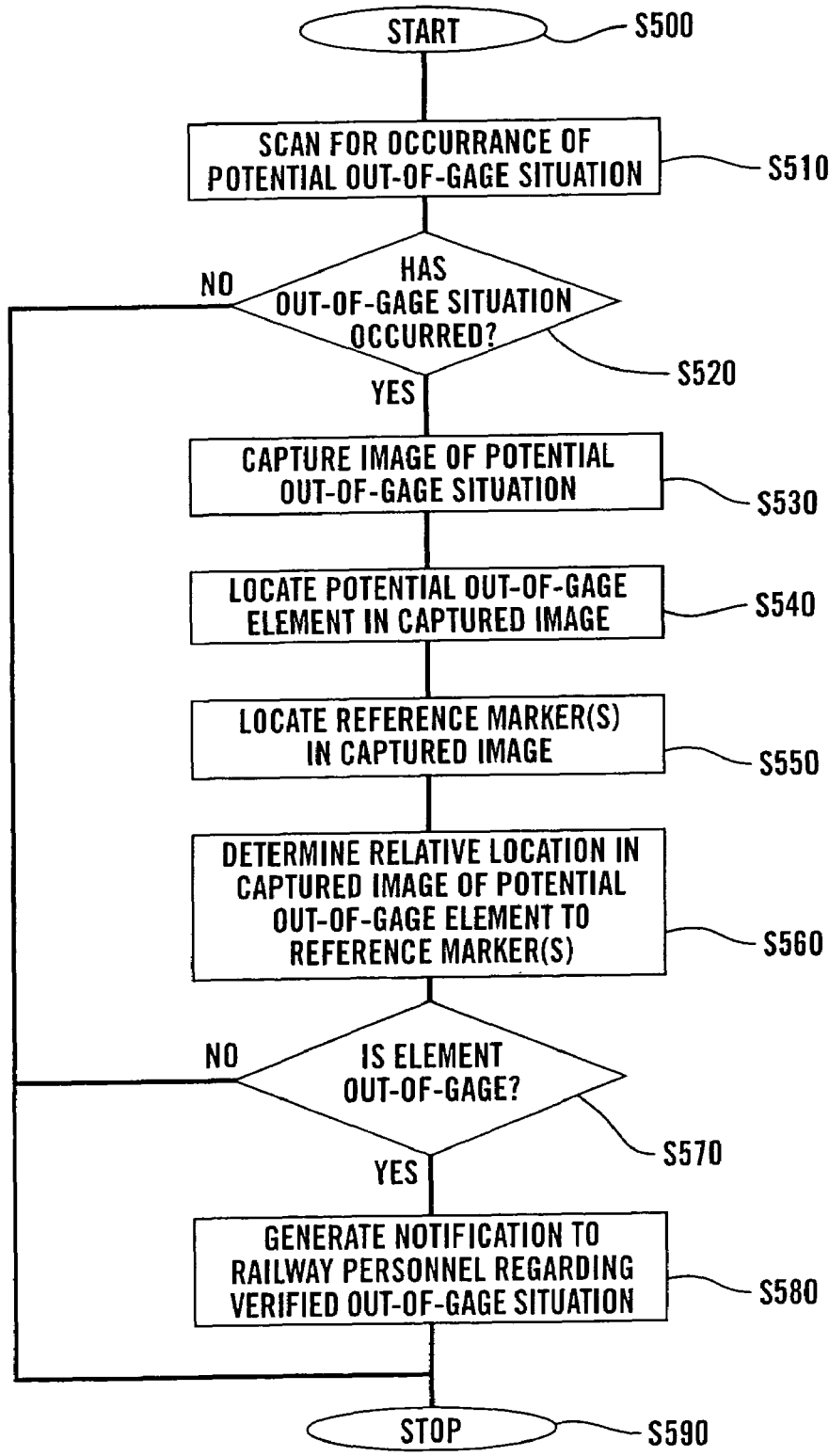
FIG. 29 is a flowchart outlining one exemplary embodiment of a method for determining if an out-of-gage situation has occurred.

FIG. 29 is a flowchart outlining one exemplary embodiment of a method for determining if a piece of rolling stock is experiencing an out-of-gage situation. As shown in FIG. 29, operation of the method begins in step S500, and continues to step S510, where a train of rolling stock of a railroad is scanned to identify any occurrences of a potential out-of-gage situation with any of the rolling stock. It should be appreciated that this can be performed using any known or later-developed method. Then, in step S520, a determination is made whether an out-of-gage situation has been detected. If so, operation continues to step S530. Otherwise, operation returns to step S510, where the train of rolling stock continues to be scanned.

In step S530, an image of the potential out-of-gage situation is captured. Next, in step S540, any potential out-of-gage elements in the captured image are located. Then, in step S550, one or more reference markers are located in the captured image. Operation then continues to step S560.

In step S560, the relative location in the captured image of any potential out-of-gage elements are determined relative to the one or more located reference markers in the captured image. Then, in step S570, a determination is made whether the potential out-of-gage element is actually out of gage. If so, operation continues to step S580. Otherwise, operation returns to step S510. In step S580, a notification is generated to the appropriate railway personnel to notify them about the verified out-of-gage situation. Operation then continues to step S590, where operation of the method ends.

It should be appreciated that, in various exemplary embodiments, the reference markers can be used to determine various types of information about various components of the piece of rolling stock as images of those components and one or more of the reference markers are captured. For example, as outlined above, a single image can be captured that includes one or more reference markers and one or more components of interest of the piece of rolling stock. That image can then be analyzed to extract information about each component of interest appearing in that captured image based on and/or relative to one or more of the reference markers appearing in that captured image.

For example, if that image is an optical image, the information can be distance of a point on one of the component(s) of interest to a point on one of the reference marker(s). This distance can be along a line extending between those points, or a perpendicular distance relative to a determined axis that passes through that point on that reference marker. Alternatively, or additionally, the information can be a dimension of that component or a feature of that component. That dimension can be based on a scale provided by one of more of the reference marker(s) appearing in that captured image and/or based on a measurement axis established or provided by such reference marker(s). Likewise, as outlined above, if the image is a thermal or other type of image that includes non-optical information, the information can be temperature or some other non-optically-based and/or non-spatial information.

Alternatively, two or more images can be captured, where each image includes one or more reference markers and one or more components of interest of the piece of rolling stock. In various exemplary embodiments, the two images can be captured by two different image capture devices, and capture two different components of interest of the piece of rolling stock, at or near the same time. Those images can then be analyzed to extract information about the components of interest appearing in those captured image based on and/or relative to one or more of the reference markers appearing in that captured image. For example, the distance between two reference markers appearing in the two images can be known. Then, for each of the two captured images, if a distance between a point on one component of interest appearing in that image and the reference marker in that image is determined, a distance between those points on the two components of interest can be determined based on the known distance between those two reference markers.

Alternatively, in various other exemplary embodiments, the two images can be captured by the same image capture device, which captures two different components of interest of the piece of rolling stock, at different times. The same one or more reference markers should also appear in the two images. Then, the positions, for optical images, temperatures, for thermal images, or other values of interest, for other non-spatial parameters, for the two components of interest, can be compared relative to those same one or more reference markers.

In contrast to both of the above-outlined alternatives, in still other exemplary embodiments, the two images can be captured by the same or different image capture devices, to capture two images of the same components of interest of the piece of rolling stock, at different times. One or more reference markers should also appear in the two images. Then, the positions, for optical images, temperatures, for thermal images, or other values of interest, for other non-spatial parameters, for the two components of interest, can be compared based on those one or more reference markers. For example, thermal images of an end cap of a wheel of a truck of a given piece of rolling stock can be captured at different times. These two images can then be calibrated and compared based on the various one or more reference markers that appear in the two captured images, to determine how the bearing temperature has changed in view of the time elapsed between the times the two images were captured.

While this invention has been described in conjunction with the exemplary embodiments outlined above, various alternatives, modifications, variations, improvements and/or substantial equivalents, whether known or that are or may be presently foreseen, may become apparent to those having at least ordinary skill in the art. Accordingly, the exemplary embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The invention claimed is:

1. An image capture system associated with a railway comprising:
 a first image capture device; and
 a first reference marker located adjacent a first rail of said railway;
 wherein the first image capture device is located and/or oriented such that the first reference marker appears in a field of view of the first image capture device; and
 wherein the first image capture device is useable to capture at least one image including the first reference marker and at least a portion of a wheel of a rail vehicle in motion to determine at least one parameter of said wheel or said rail vehicle.

2. The image capture system of claim 1, further comprising a second reference marker located adjacent to the first reference marker and in the field of view of the first image capture device.

3. The image capture system of claim 1, wherein the first reference marker is adapted to be interconnected to said first rail and/or at least one other component of said railway.

4. The image capture system of claim 1, wherein the first reference marker is located at a substantially fixed position near said first rail.

5. The image capture system of claim 2, wherein the first reference marker is adapted to be interconnected to said first rail and/or at least one other component of said railway and the second reference marker is located at a substantially fixed position.

6. The image capture system of claim 1, further comprising a second image capture device located and oriented such that a portion or component of said rail vehicle appears in a field of view of the second image capture device.

7. The image capture system of claim 1, further comprising:
 a second image capture device;
 a second reference marker located adjacent a second rail of said railway; and
 wherein the second image capture device is located and/or oriented such that the second reference marker appears in a field of view of the second image capture device.

8. The image capture system of claim 1, further comprising a central processing unit in communication with the first image capture device.

9. The image capture system of claim 1, wherein the at least one image is captured and utilized to determine at least one of a wheel hollowing condition, wheel flange height, wheel flange width, wheel rim thickness, wheel flange angle, the back-to-back distance between a pair of wheels connected by an axle, the lateral position of a wheel along the first rail, axle straightness, end cap center-ness, coupler height, a leaning vehicle, the condition of a vehicle's suspension, and an out-of-gage condition.

10. An image capture system associated with a railway comprising:
 an image capture means; and
 a reference means located in proximity to a rail of said railway;
 wherein the image capture means is oriented such that the reference means appears in a field of view of the image capture means; and
 wherein the first image capture means is useable to capture at least one image including the reference means and at least a portion of a wheel of a rail vehicle in motion to determine at least one parameter of said wheel or said rail vehicle.

11. The image capture system of claim 10, wherein the at least one image is captured and utilized to determine at least one of a wheel hollowing condition, wheel flange height, wheel flange width, wheel rim thickness, wheel flange angle, the back-to-back distance between a pair of wheels connected by an axle, the lateral position of a wheel along the rail, axle straightness, end cap center-ness, coupler height, a leaning vehicle, the condition of a vehicle's suspension, and an out-of-gage condition.

12. A method for obtaining information about a rail vehicle and/or at least one of its components comprising:
   passing said rail vehicle along a railroad track through an image capture region, the image capture region having at least one reference marker positioned about at least one rail of said railroad track in a field of view of at least one image capture device; and
   utilizing the image capture device to capture a first image containing at least a portion of the reference marker and at least a first portion or component of said rail vehicle while said rail vehicle is in motion to determine at least one parameter of said rail vehicle.

13. The method of claim 12, further comprising analyzing the first image to determine information about at least one of said first portion or component of said rail vehicle and said rail vehicle.

14. The method of claim 12, further comprising utilizing the image capture device to capture a second image containing at least a portion of the reference marker and at least a second portion or component of said rail vehicle while said rail vehicle is in motion.

15. The method of claim 14, further comprising comparing the first image and the second image to determine information about at least one of said rail, said first portion or component of said rail vehicle, said second portion or component of said rail vehicle and said rail vehicle.

16. The method of claim 14, further comprising:
   analyzing the first image to obtain information about at least one of said rail, said first portion or component of said rail vehicle, and said rail vehicle;
   analyzing the second image to obtain information about at least one of said rail, said second portion or component of said rail vehicle, and said rail vehicle; and
   comparing the information obtained from the analysis of the first image to the information obtained from the analysis of the second image to determine the condition of at least one of said rail, said first portion or component of said rail vehicle, said second portion or component of said rail vehicle, and said rail vehicle.

17. The method of claim 14, further comprising:
   analyzing the first image to obtain information about at least one of said rail, said first portion or component of said rail vehicle, and said rail vehicle;
   analyzing the second image to obtain information about at least one of said rail, said second portion or component of said rail vehicle, and said rail vehicle; and
   combining the information obtained from the analysis of the first image to the information obtained from the analysis of the second image to determine the condition of at least one of said rail, said first portion or component of said rail vehicle, said second portion or component of said rail vehicle, and said rail vehicle.

* * * * *